United States Patent
Vonesh et al.

(10) Patent No.: US 6,673,102 B1
(45) Date of Patent: Jan. 6, 2004

(54) COVERED ENDOPROSTHESIS AND DELIVERY SYSTEM

(75) Inventors: Michael J. Vonesh, Flagstaff, AZ (US); Joseph R. Armstrong, Flagstaff, AZ (US); Edward H. Cully, Flagstaff, AZ (US); Margaret L. Gallegos, Flagstaff, AZ (US)

(73) Assignee: Gore Enterprises Holdings, Inc., Newark, DE (US)

( * ) Notice: Subject to any disclaimer, the term of this patent is extended or adjusted under 35 U.S.C. 154(b) by 0 days.

(21) Appl. No.: 09/489,604

(22) Filed: Jan. 20, 2000

Related U.S. Application Data

(63) Continuation-in-part of application No. 09/235,219, filed on Jan. 22, 1999.

(51) Int. Cl.[7] .................................................. A61F 2/06
(52) U.S. Cl. ..................... 623/1.13; 623/1.11; 623/1.44
(58) Field of Search ............................. 623/1.11, 1.12, 623/1.13, 1.14, 1.15, 1.16, 1.17, 1.18, 1.19, 1.2, 1.21, 1.22, 1.44–1.46; 656/108, 191, 194, 195, 198

(56) References Cited

U.S. PATENT DOCUMENTS

| | | | |
|---|---|---|---|
| 3,953,566 A | 4/1976 | Gore | 264/288 |
| 3,962,153 A | 6/1976 | Gore | 260/2.5 R |
| 4,096,227 A | 6/1978 | Gore | 264/210 R |
| 4,187,390 A | 2/1980 | Gore | 174/102 R |
| 4,877,661 A | 10/1989 | House et al. | 428/34.9 |
| 4,902,423 A * | 2/1990 | Bacino | 210/500.36 |
| 5,476,589 A | 12/1995 | Bacino | 210/500.36 |
| 5,545,211 A * | 8/1996 | An et al. | 623/1.2 |
| 5,575,818 A | 11/1996 | Pinchuk | 623/1 |
| 5,620,763 A | 4/1997 | House et al. | 428/36.9 |
| 5,683,453 A | 11/1997 | Palmaz | 623/1 |
| 5,718,973 A | 2/1998 | Lewis et al. | 428/36.5 |
| 5,735,892 A | 4/1998 | Myers et al. | 623/1 |
| 5,800,519 A | 9/1998 | Sandock | 623/1 |
| 6,015,431 A | 1/2000 | Thornton et al. | 623/1 |
| 6,059,822 A | 5/2000 | Kanesaka et al. | 623/1 |
| 6,156,064 A * | 12/2000 | Chouinard | 623/1.44 |

FOREIGN PATENT DOCUMENTS

| | | |
|---|---|---|
| EP | 0 714 487 B1 | 8/1994 |
| EP | 0 645 125 A1 | 3/1995 |
| EP | 0 792 627 A2 | 9/1997 |
| EP | 0 855 170 A2 | 7/1998 |
| EP | 0 857 471 A2 | 8/1998 |
| EP | 0 880 948 A1 | 12/1998 |
| GB | 1355373 | 5/1971 |
| GB | 1506432 | 3/1975 |
| WO | 97/21401 | 6/1997 |
| WO | 98/27894 | 7/1998 |

* cited by examiner

Primary Examiner—Vy Q. Bui
(74) Attorney, Agent, or Firm—David J. Johns

(57) ABSTRACT

The present invention is an improved endovascular device particularly useful for use in transjugular intrahepatic portosystemic shunt (TIPS) procedures. The device employs a two-part stent-graft construction that provides a low permeability membrane to line the shunt and an uncovered stent portion designed to reside in the portal vein. The device provides numerous benefits over previous stents and stent-grafts used in TIPS procedures, including being more compact to deliver, being easier to accurately deploy, a controlled compacted surface with tucked apices, an improved stent winding pattern, and being more flexible in delivery and use.

18 Claims, 14 Drawing Sheets

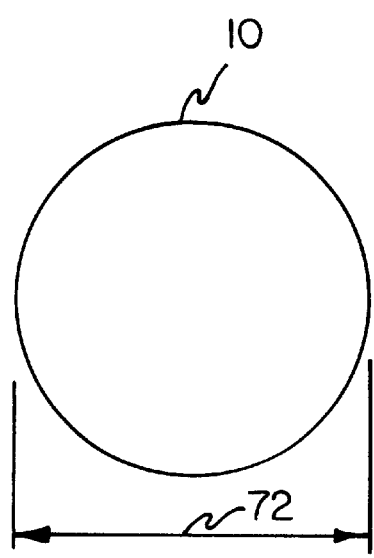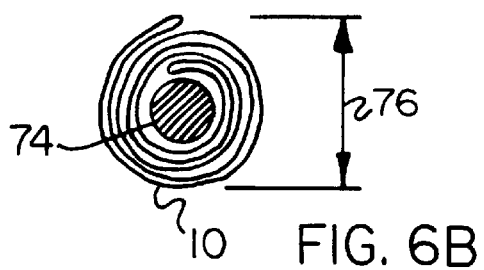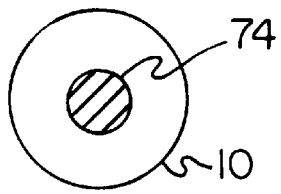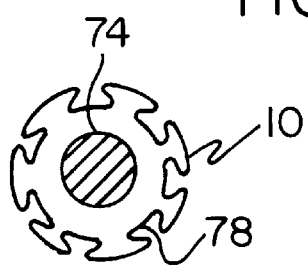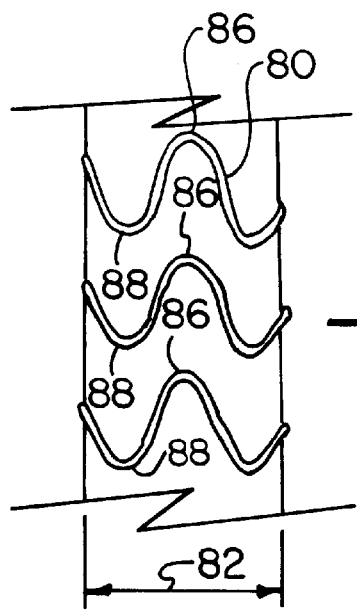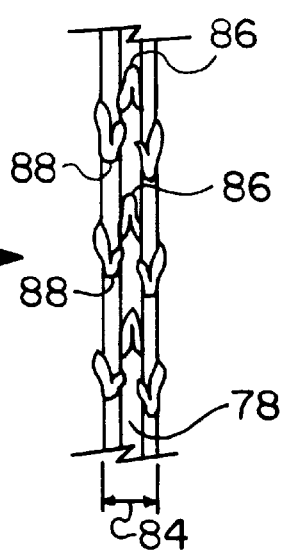

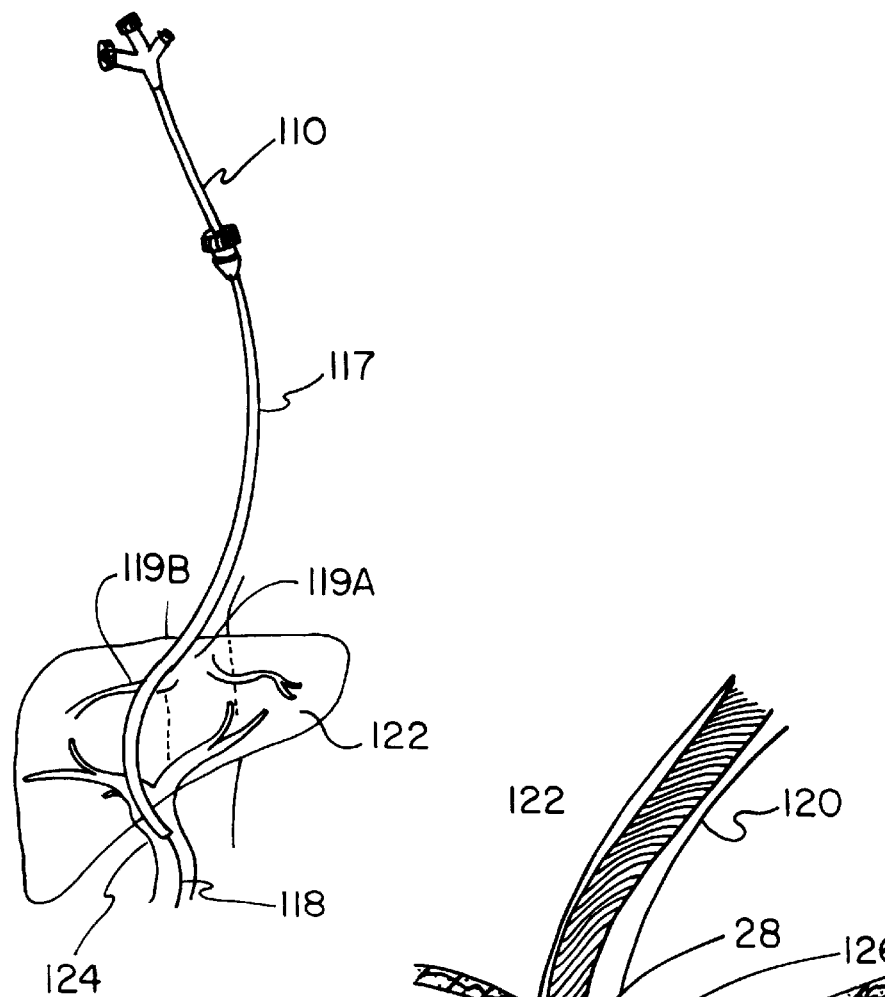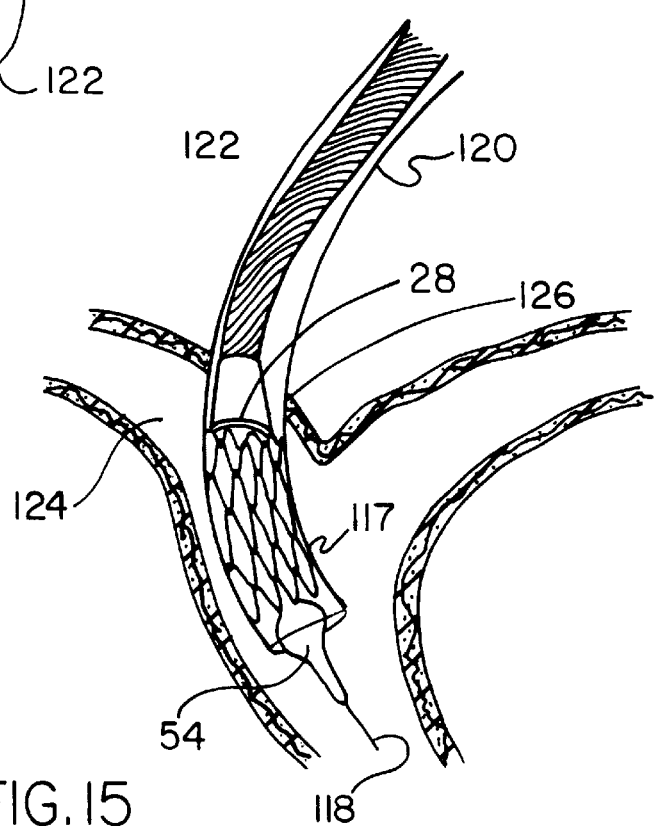
FIG. 14
FIG. 15

COVERED ENDOPROSTHESIS AND DELIVERY SYSTEM

RELATED APPLICATIONS

The present application is a continuation-in-part of co-pending U.S. patent application Ser. No. 09/235,219, filed Jan. 22, 1999.

BACKGROUND OF THE INVENTION

1. Field of the Invention

The present invention relates to endoprostheses such as stents and stent-grafts, and particularly to endoprostheses that are suitable for use in transjugular intrahepatic portosystemic shunt (TIPS) applications.

2. Description of Related Art

It is known that diseased or damaged liver tissue may increase the resistance to hepatic perfusion resulting in excessive and often dangerous fluid pressure increases in the portal vascular circulation. This condition can lead to gastrointestinal variceal hemorrhage and pathological conditions such as ascites.

In order to decompress the portal circulation, a transjugular intrahepatic portosystemic shunt (TIPS) may be created through the liver tissue by connecting the portal vein to the inferior vena cava via the hepatic vein. This procedure first forms a fairly large puncture (for instance, using a 16 or 18 gauge needle) directly through the liver to allow direct flow between the portal vein and the hepatic vein. Next the puncture is lined with a stent (for example, an 8–12 mm stent) to form a shunt. The TIPS procedure has proven to be safe and effective at decompressing the portal system and in controlling acute variceal hemorrhage. A summary of TIPS procedures using unlined Palmaz balloon-expandable stents (available from Cordis Corp., Miami Lakes, Fla.) is provided in Zemel, et al., "Technical Advances in Transjugular Intrahepatic Portosystemic Shunts," 12 *RadioGraphics* 615–622 (1992).

Unfortunately, for many patients conventional TIPS procedures may provide fairly short-lived improvements. Stenosis or occlusion may occur in up to half of all patients within 6 months following TIPS creation. Blockage of the shunt normally occurs due to pseudointimal formation or intimal hyperplastic response.

In the article by Nishimine, et al., "Improved Transjugular Intrahepatic Portosystemic Shunt Patency with PTFE-Covered Stent-Grafts: Experimental Results in Swine," 196 *Radiology* 341–347 (1995), the authors hypothesize that shunt patency might be improved if flowing blood could be separated from leaking bile, the exposed surface of liver parenchyma, and the injured hepatic vein. In that article the authors describe a device that comprises a thin-walled polytetrafluoroethylene (PTFE) graft (available from W. L. Gore & Associates, Inc., Flagstaff, Ariz.) having single-body Gianturco-Rosch Z-stents (available from Cook Inc., Bloomington, Ind.) mounted on each end for anchorage. Once mounted in place, the authors then deployed one or two WALLSTENT stents (available from Schneider Inc., Minneapolis, Minn.) within the PTFE graft to provide mid-shunt radial support. The authors reported that a PTFE-covered stent-graft provided improved TIPS patency verses uncovered stents in a porcine model. However, the authors also indicated that accurate stent-graft placement was important in order to maintain patency, since occlusion continued to occur when a stent-graft was misplaced in the shunt or if a portion of the intrahepatic tract between the portal vein and the hepatic vein was otherwise left unlined.

Nishimine et al. also reported that the two-step deployment of their stent-grafts (that is, deploying a graft with anchoring stents first and then separately deploying WALLSTENT stents within the graft as a second procedure) was "cumbersome and technically challenging." Nevertheless, as the authors explained, this two-part procedure was necessary in order to allow placement of the stent and graft combination through a small 10-French (F) (3.3 mm) sheath.

Accordingly, a lined or otherwise covered stent-graft device would appear to be useful in helping to maintain patency in TIPS procedures. However, a number of problems are presented to someone attempting to provide an improved TIPS stent-graft.

First, as Nishimine et al. reported, small profile delivery of a stent-graft device is difficult to accomplish in a single step. Generally percutaneous delivery of a stent or stent-graft requires the device to be delivered at no more than 13-F (4.3 mm). While Nishimine et al. achieved delivery of a stent and graft through a 10-F sheath, this was accomplished through a cumbersome and challenging two-step procedure in which the separate devices were combined in-situ. Other authors have reported delivering stent and graft combined structures in one-step, but have required larger introductory profiles to do so, on the order of about 14-F to 16-F (4.7–5.3 mm): Haskal, et al, "PTFE Encapsulated Endovascular Stent-Graft for Transjugular Intrahepatic Shunts: Experimental Evaluation," Radiology: 205 (1997); Behesti, et al. "Technical Considerations in Covering and Deploying a Wallstent Endoprosthesis for the Salvage of a Failing Transjugular Intrahepatic Portosystemic Shunt," JVIR: 9 (1998).

Second, also as Nishimine et al. reported, accurate device sizing and placement may be critical in order to successfully avoid a biological response resulting in stenosis or occlusion. Premature device occlusion or shunt malfunction may be caused by a variety of conditions, including: failing to maintain proper flow into and out of the shunt device; failing to position the device to completely cover the intrahepatic tract between the portal and hepatic veins; or extending the device too far in the portal circulation or inferior vena cava.

Third, it appears important that the graft portion of the device inhibits seepage of bile and other thrombogenic or mitogenic substances into the blood system. Maintaining bile-exclusion while also seeking to use very thin graft materials in order to achieve small device delivery profiles presents a critical design challenge.

Fourth, the stent-graft also needs to have sufficient structural strength to resist distortion during use. Nishimine et al. report that protrusion of tissue through an uncovered stent structure may result in up to 40% of pseudointimal thickness. The present inventors believe that this tissue encroachment may be one of the reasons that uncovered stent structures do not perform very well. While any cover should limit the extent of tissue protruding through the stent structure, it is believed desirable to provide a cover with sufficient strength that it will resist distortion from the inward force of tissue protrusion. Thus, the choice of cover material, as well as its method of attachment to the underlying stent, present design challenges. The stent component also needs sufficient radial strength to prevent the stent-graft from significantly narrowing or collapsing under pressure from scar or fibrotic proliferation. Again, with respect to both the stent and the graft components, the amount of radial strength provided must be balanced against the desire for thin graft membranes and minimal stent size needed to create an overall device with small profile. Also, a desired attribute in the TIPS procedure is that the endoprosthesis is flexible in order to accommodate the tortuous intrahepatic pathway.

SUMMARY OF THE INVENTION

The present invention is an improved endoprosthetic device specifically designed to line an intrahepatic shunt formed within liver tissue in order to maintain its effectiveness. The present invention addresses the endoprosthesis itself, as well as delivery and deployment apparatus, including associated catheters, capture and restraining means, and other related apparatus. The device of the present invention comprises an endoprosthesis designed to be deployed in the transjugular intrahepatic portosystemic shunt (TIPS) procedure. The endoprosthesis of the present invention comprises a two-part construction having a first, covered, segment that is designed to be positioned within the intrahepatic tract and hepatic vein and a second, uncovered, segment that is designed to reside in the portal vein upstream of the shunt. The endoprosthesis of the present invention provides a unique stent and graft combination that combines a self-expanding stent with high radial strength with a thin-walled graft material that is resistant to permeation by bile and other fluids.

The endoprosthesis of the present invention has numerous desirable features. First, the covered segment employs a thin bile exclusionary graft material that protects the shunt from bile infiltration while maintaining small wall thicknesses. Second, the device has a unique one-piece construction that allows it to be easily and accurately placed within the intrahepatic tract. Third, the present invention provides a unique multi-stage deployment procedure that again aids in the accurate placement of the endoprosthesis. Fourth, the device is highly flexible, aiding in its positioning and deployment. Fifth, the device is highly compactable, again aiding its deployment and minimizing device profile. Sixth, the device employs a unique self expanding stent pattern that is believed to be easier to manufacture, easier to deploy, and safer to use than alternative stent patterns. These and other benefits of the present invention will be appreciated from review of the following description.

DESCRIPTION OF THE DRAWINGS

The operation of the present invention should become apparent from the following description when considered in conjunction with the accompanying drawings, in which:

FIG. 6a is an end view of an endoprosthesis of the present invention at its deployed diameter;

FIG. 6b is an end view of the endoprosthesis of FIG. 6a, with the endoprosthesis shown compacted by folding and rolling the endoprosthesis about a central catheter shaft;

FIG. 6c is an end view of the endoprosthesis of FIG. 6a, with the endoprosthesis shown compacted by radially compressing the endoprosthesis about a central catheter shaft;

FIG. 6d is an end view of the endoprosthesis of FIG. 6a, with the endoprosthesis shown radially compacted by folding into pleats of the endoprosthesis about a central catheter shaft;

FIG. 7 is a side elevation view of an endoprosthesis of the present invention shown in its deployed diameter and in a compacted, pleated diameter;

FIG. 14 is a side elevation view of a compacted endoprosthesis of the present invention shown advanced into a portal vein;

FIG. 15 is a side elevation view of a compacted endoprosthesis of the present invention shown confined within a hemostatic sheath and located at an intrahepatic juncture site in a portal vein;

DETAILED DESCRIPTION OF THE INVENTION

The present invention is an improved implantable endoluminal device, and especially such a device for establishing and maintaining an intrahepatic portosystemic shunt. As is explained in greater detail below, typically this procedure is performed endoluminally through the jugular vein, connecting the portal vein to the inferior vena cava by way of hepatic vein. As a result, the procedure is commonly referred to as being a "transjugular intrahepatic portosystemic shunt" or abbreviated "TIPS" or "TIPSS." It should be appreciated, however, that a shunt through the liver between the portal vein and the vena cava may be accomplished by other methods and that the endoprosthesis devices of the present invention are not limited in application to transjugular insertion. As such, the term "intrahepatic portosystemic shunt" as used herein is intended to include any procedure whereby pressure is relieved in the portal vein by way of a shunt from the portal to the systemic systems.

As has been explained, typically a shunt is established creating a large tract (for instance, by puncturing with a 16 or 18 gauge needle and then ballooning to about 10 mm) directly through the liver to allow connection between the portal vein and the hepatic vein. Following ballooning, the shunt is generally maintained by lining the puncture with an uncovered stent. The TIPS procedure has proven to be safe and effective at decompressing the portal system and in controlling acute variceal hemorrhage. Unfortunately, for many patients conventional TIPS procedures may provide fairly short-lived improvements. Stenosis or occlusion may occur in a significant number of patients. Blockage of the shunt normally occurs due to thrombosis, pseudointimal formation, or intimal hyperplastic response. While covered stents have been employed with some improvement in subsequent occlusive response, these previous covered stent devices have been difficult to properly position, have had excessively large insertion profiles, and/or are ineffective at bile exclusion—bile being linked to increased hyperplastic response.

The present invention addresses all of these deficiencies of previous stent devices by providing an endoprosthesis stent-graft combination that has a small introductory profile, is easily positioned and deployed within the shunt, and employs a cover that is highly resistant to bile permeation.

Figure 1:
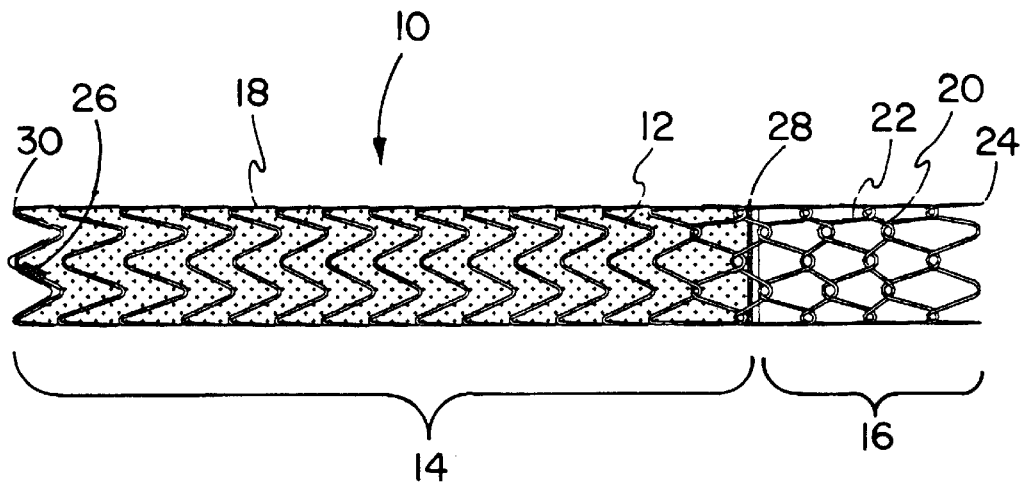
FIG. 1 is a side elevation view of one embodiment of an endoprosthesis of the present invention.

Shown in FIG. 1 is one embodiment of an endoprosthesis 10 of the present invention. The endoprosthesis comprises a two-part stent element 12 having a first segment 14 and a second segment 16. A cover 18 is provided along the length of the first segment 14, while the second segment 16 is left uncovered.

The first segment 14 and the cover 18 are adhered together (for instance by an adhesive and/or by a wrap of an adhered film) to maintain the position of the cover 18 on the endoprosthesis 10. The attachment of the cover to the stent element 12 also prevents the first segment 14 from excessively longitudinally elongating when longitudinal tension is applied to the endoprosthesis 10. It is believed preferable that the cover 18 line the interior of the stent element 12, as shown, but acceptable results may also be achieved with the cover 18 placed on the outside of the stent element 12, with the cover being placed both inside and outside of the stent element 12, or with the stent element 12 being embedded within the cover 18. As such, the term "cover" as used herein is intended to include any generally continuous material that is placed inside of and/or placed outside of and/or mounted integrally with the stent element 12 of the present invention.

As will become clear from the following description, the second segment 16 of the stent is left uncovered to permit its permanent deployment within the portal vein and thereby allow perfusion of portal venous branches through the interstices of 16. In order to prevent the second segment 16 from undergoing uncontrolled longitudinal elongation, a different stent pattern is employed along this uncovered segment. In this embodiment an interlocked (or "chain-linked") stent pattern 20 is used that prevents the second segment 16 from excessively longitudinally elongating beyond a predetermined desired length. In the interlocked stent pattern 20 shown, a single wire 22 is employed that is wrapped from the cover 18 to a distal end 24 of the endoprosthesis 10 and then back to the cover 18. This pattern allows the wire 22 to be terminated within the cover 18 and avoids having a loose end of the wire 22 exposed at distal end 24 of the endoprosthesis 10. This wrapping pattern is explained in greater detail with regard to FIG. 3, below.

In order to facilitate placement of the endoprosthesis 10 device, a series of radiopaque markers 26, 28 are provided along the length of the endoprosthesis. Marker 26 identifies proximal end 30 of the endoprosthesis 10 and marker 28 identifies the junction between the first segment 14 and the second segment 16 of the endoprosthesis 10. By employing marker 28 as a circumferential band that entirely or substantially marks the circumference of the endoprosthesis 10, this further facilitates correct placement of the endoprosthesis 10.

The stent element 12 may be formed from a variety of wire materials, including stainless steel, nickel-titanium alloy (nitinol), tantalum, elgiloy, various polymer materials, such as poly(ethylene terephthalate) (PET) or polytetrafluoroethylene (PTFE), or bioresorbable materials, such as levorotatory polylactic acid (L-PLA) or polyglycolic acid (PGA). The preferred material comprises a superelastic material, such as nitinol metal, that will withstand tight compression in a compacted configuration (diameter) and then self-expand to a deployed configuration (diameter) once released in place. Alternatively, the stent element 12 of the present invention may be constructed from a material (e.g., stainless steel) that can be mechanically enlarged in place, such as through balloon expansion.

For application in a TIPS procedure, the endoprosthesis 10 of the present invention would typically have dimensions as follows: a length of about 5 to 12 cm, with a length of about 6 to 10 cm being preferred; a deployed diameter of about 6 to 14 mm, with a diameter of about 8 to 12 mm preferred; and a wall thickness (comprising both the cover 18 and the stent element 12) of about 0.1 to 1.0 mm, with about 0.1 to 0.6 mm being preferred. While the dimension "diameter" is used herein, it should be understood that this dimension is intended to define the average cross-sectional dimension of the device and is not intended to limit the present invention to devices with circular cross-sectional shapes. The device may also have multiple diameters, with the diameter of section 16, for example, being larger (or smaller) than the diameter of section 14. One or both of the sections 14, 16 may also be tapered or otherwise adjusted in dimensions.

The endoprosthesis 10 itself will preferably have a compacted dimension of less than or equal to 16 French (5.3 mm), and more preferably a compacted dimension of less than or equal to 12 F (about 4.0 mm), and even more preferably a compacted dimension of less than or equal to 10 F (3.3 mm) or even 9 F (3.0 mm) or 8 F (2.7 mm) or less. In order to be delivered percutaneously, the endoprosthesis and its deployment apparatus should have a diameter of less than about 13 F (4.3 mm), and more preferably less than or equal to 10 F (3.3 mm). "French" measurements used herein define the size of a hole through which a device will pass. For example, a device with a measurement of "10 French" will pass through a 10 French hole (which has a diameter of 3.3 mm). Again, the device need not have a circular cross-section in order to pass through a circular 10 French hole so long as the hole is large enough to accommodate the widest cross-section dimension of the device.

The first segment 14 of the endoprosthesis 10 will typically comprise about 50 to 90 percent of the entire length of the endoprosthesis. Accordingly, the first segment 14 will normally be about 4 to 8 cm in length and the second segment 16 will normally be about 1 to 3 cm in length.

The preferred stent element 12 is constructed from a superelastic nitinol metal with the following properties: having alloy percentage of about 51% nickel, about 49% titanium (for example, SE 508 available from Nitinol Devices & Components, Fremont, Calif., USA); being 40–45% cold worked; having a tensile modulus of approximately 35 to 70×10$^6$ kPa; being electopolished; and having a wire diameter of about 0.15 to 0.50 mm, and preferably about 0.25 to 0.30 mm.

The cover 18 performs a number of functions in the endoprosthesis 10 of the present invention. First, the cover 18 prevents extrusion of liver tissue through the stent element so as to help maintain the full desired diameter of the shunt. Second, as has been noted, the cover 18 helps to maintain the dimensions of the endoprosthesis and prevents uncontrolled elongation of the stent element. Third, it is believed to be highly desirable for the cover 18 to reduce or eliminate bile from permeating into the shunt. Fourth, the cover allows bending of segment 14 without kinking or compromising the luminal surface of the device. Based upon the medical literature, the inventors believe that bile permeation into the shunt may contribute to hyperplastic response and premature occlusion. It is also desirable that the cover 18 provides all of these benefits while contributing minimal additional profile to the endoprosthesis device.

To this end, it is desirable to provide a cover material that has the following properties: longitudinal tensile strength when mounted in the device of about 5 to 20 Kgf, and preferably about 10 to 15 Kgf; a permeability as quantified by a Gurley Number of greater than about 60 seconds per 100 cc of air per one (1) cm$^2$ of material; a thickness of about 0.05 to 0.25 mm, with a thickness of about 0.10 to 0.20 mm preferred; a water entry pressure of about 5 to 15 psi (34 to 102 kPa) or more, with 7 to 9 psi (48 to 62 kPa) or more preferred. Test procedures used to establish these values are described in the Examples below.

As the terms "bile exclusionary," "resistant to bile permeation," "bile resistant," and similar terms are used herein, these are intended to encompass any cover that has a Gurley Number of greater than about 60 seconds per 100 cc air per a cm$^2$ material. More preferably, the Gurley Number is greater than about 70, 80, 90, 100 or more seconds per 100 cc of air per 1 cm$^2$ of material.

The preferred cover 18 material comprises a fluoropolymer and especially a fluoropolymer comprising expanded polytetrafluoroethylene (PTFE). For example, a cover may be constructed by forming an ultra-thin walled expanded PTFE base tube by methods described in British Patents 1,355,373, 1,506,432, published PCT Application WO 95/05555, and in U.S. Pat. Nos. 3,953,566, 3,962,153, 4,096,227, 4,187,390, 4,902,423, 5,718,973, 5,735,892, and 5,620,763, all of which are incorporated herein by reference. This process produces an expanded PTFE tube having a microstructure of polymeric nodes connected by polymeric fibrils and defining void spaces therein.

The extruded ultra-thin walled tube preferably has a wall thickness of about 0.05 to 0.30 mm, with a preferred wall thickness of about 0.05 to 0.2 mm. The tube preferably has a nominal fibril length of about 5 to 50 micron, with a preferred fibril length of about 15 to 35. Fibril length may be determined through conventional methods, such as Section 8.2.1.3 of ANSI/AAMI VP20-1994, incorporated by reference.

Over the extruded ultra-thin walled tube an expanded PTFE film is helically wrapped. The film may be manufactured in the following manner: PTFE fine powder is blended with a hydrocarbon lubricant and paste extruded through a flat die. The resulting tape is calendered to approximately 50% of is original thickness. Next, the tape is then heated to volatilize the hydrocarbons. The resulting dried tape is then heated to about 300° C., expanded at a ratio of 25:1 and then expanded again at a ratio of 8:1, and then sintered at a temperature of about 370° C. to achieve the desired properties.

This produces a low permeability film, with preferred properties of about 0.005 to 0.025 mm in thickness, with a more preferred thickness of about 0.010 to 0.015 mm (as measured by a Mitutoyo Snap Gauge Model Number 2804-10). The film preferably has a fibril length of approximately 50 to 100 micron, with a preferred fibril length of about 70 to 80 microns. The film further has a methanol bubble point of about 10 to 40 kPa, and more preferably a bubble point of about 20 to 30 kPa. Alternatively, a film as described in U.S. Pat. No. 5,476,589 to Bacino, incorporated by reference, may be employed.

Bubble point may be determined by placing the film in a one inch (2.54 cm) diameter round clamp and completely wetting the sample out with methanol from above. Pressure is then applied slowly (at the approximate rate of 40 kPa/min) to the bottom side of the wet out sample until bubbles appear on the other side of the sample. The pressure at which the first bubble appears is designated as the "bubble point."

Finally, the film has a Frazier permeability of about 0.5 to 3 cm$^3_{air}$/sec/cm$^2_{material}$ @ 125 Pa back pressure, with a preferred Frazier permeability of about 0.5 to 1.5 cm$^3_{air}$/sec/cm$^2_{material}$ @ 125 Pa back pressure. Frazier permeability may be determined by placing a sample of material (referred to as a "membrane") to be tested on a 25.4 mm diameter circular clamp. One side of the clamp is sealed such that gauge pressure can be supplied to one side of the membrane and flow rates through the membrane can be measured. Ambient air (20°C.±3 C.) is slowly increased on one side of the membrane to 125 Pa. The flow of air through the membrane is measured, and expressed in units of cubic centimeters of air (cm$^3_{air}$) flowing through a square centimeter of material (cm$^2_{material}$) in a second (s) with a back pressure of 125 Pa.

To assemble the material of the cover 18, the extruded ultra thin wall base tube is mounted over a stainless steel mandrel with approximately the same outer diameter as the inner diameter of the base tube. The film is slit to 0.75 inches (19 mm) wide and then helically wrapped in approximately 6 layers onto the ultra-thin walled base tube (with an overlap of about 16 mm for each wrap of the tube). The composite construction is cooked in an air convection oven for about 15 minutes at about 370° C.

After the composite tube has cooled, "stored length" may be imparted into the wrapped tube by deforming or bending the fibrils of the expanded PTFE node and fibril microstructure and setting the material in this configuration, such as in the following manner. The stored length is imparted by compressing ("scrunching") the graft along the mandrel longitudinally up until a point where the graft material begins to buckle. After this compression, the construction is heated treated at about 320° C. for about 5 minutes. In order to achieve greater stretch, the base tube can be over-wrapped with a thin ePTFE film layer prior to scrunching. This over-wrap resists buckling of the tube, allowing more longitudinal compression to be imparted. After the construction is heat treated, the over-wrap is then unwrapped and removed, and the composite is carefully removed from the mandrel. Stored length may also be imparted to the device after the stent has been attached. This can be accomplished through a similar process except an additional 320° C. heat treatment cycle for approximately 15 minutes is performed after stent attachment and compression.

After "stored length" has been imparted to the tube (such as through the above described "scrunching" process), the stent can be slid coaxially over the PTFE film wrapped tube. The stent is preferably constructed of a helical pattern as described and illustrated herein with no interconnects from row-to-row, such that the stent can bend freely. The wrapped tube and stent are then mounted onto a stainless steel mandrel. An expanded PTFE tube (e.g., a GORE-TEX® Vascular Graft, available from W. L. Gore and Associates, Inc., Flagstaff, Ariz., USA) can be sandwiched between the wrapped tube and the undersized stainless steel mandrel to function as a cushioning layer. The apices of the stent are aligned as necessary, and a porous composite film of FEP and PTFE are wrapped over the construction in approximately 5 overlapping layers, with the side of the film containing FEP toward the lumen of the graft. Alignment of the stent apices can be accomplished through use of a filament threaded through apices of adjacent rows of first segment 14.

The cover 18 is preferably attached to the stent element 12 by adhering the two together through use of a suitable adhesive, such as fluorinated ethylene propylene (FEP), polyurethane, cyanoacrylates, etc. Additionally, the materials may be bonded together through heat treatment (such as, sintering of the materials together) or through use of a wrap (for instance a tube, tape, or membrane) around the outside of the stent and cover (either continuous or discontinuous) that is adhered through either a thermoplastic or thermoset adhesive to the stent and cover. Alternatively, the stent may also be coated with a thermopolymer or thermoset adhesive and the cover bonded by reflowing or setting the polymer coating.

The FEP-coated porous expanded PTFE composite film is made by a process that comprises the steps of:
a) Contacting a porous PTFE film with another layer which is preferably a film of FEP or alternatively of another thermoplastic polymer;
b) Heating the composition obtained in step a) to a temperature above the melting point of the thermoplastic polymer;
c) Stretching the heated composition of step b) while maintaining the temperature above the melting point of the thermoplastic polymer; and
d) Cooling the product of step c).

The FEP adhesive coating on the porous expanded PTFE film may be either continuous (non-porous) or discontinuous (porous), depending primarily on the amount and rate of stretching, the temperature during stretching, and the thickness of the adhesive prior to stretching. The preferred composite film has a thickness of about 0.0004" (0.01 mm), a methanol bubble point of about 1.5 psi (10 kPa), a Frazier number of about 21 $ft^3_{air}/min/ft^2_{material}$ @ 0.5"$H_2O$ back pressure (10.7 $cm^3_{air}/sec/cm^2_{material}$ @ 125 Pa back pressure), and an approximate weight ratio of FEP to PTFE of 18%.

Weight ratio is calculated by using 2.1 g/cc as the density of FEP and 1.5 g/cc as the density of dried tape. The total mass of FEP going into the expansion process is divided by the total mass of dried PTFE tape going into the expansion process.

After this wrap, the construction is cooked in an air convection oven at about 320° C. for 15 minutes. After cooking, the construction is cooled to ambient temperature and removed from the mandrel.

As has been noted, it is believed to be desirable to exclude bile and other biological liquids from permeating through the cover 18. The above described cover 18 construction produces a material that the inventors believe is significantly resistant to transmural fluid (bile) permeation. The ability of a material to exclude bile can be approximated by measuring the Gurley Number of the material. The test for this procedure is detailed in the Examples, below.

The markers 26, 28 may comprise any suitable radiopaque material that will appear on a fluoroscope or similar device. Suitable materials may include: metal (such as gold, iridium, platinum, or stainless steel); or filled polymers (such as carbon filled expanded polytetrafluoroethylene, or barium filled FEP).The preferred markers 26, 28 comprise greater than 99.9% gold.

Figure 2:
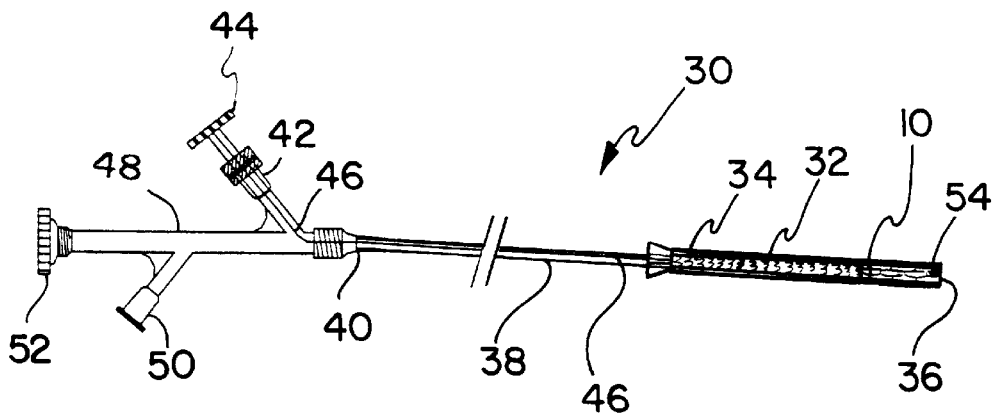
FIG. 2 is a side elevation view of an endoprosthesis of the present invention shown mounted in its delivery apparatus.

FIG. 2 illustrates one embodiment of the deployment apparatus 30 that may be used to install an endoprosthesis 10 of the present invention. This deployment apparatus 30 comprises: an introducing (or packaging) sleeve 32; a constraining sleeve 34; a distal shaft 36; a proximal shaft 38; a strain relief 40; a deployment port 42; a deployment knob 44 mounted within the deployment port 42 that is connected to a deployment line 46 attached to a constraining sleeve 34 surrounding the endoprosthesis 10; a side arm adapter 48; a flushing port 50; and a guidewire port 52. A radiopaque marker 54 may be provided on the distal shaft 36 to aid in the remote positioning of the endoprosthesis 10. The operation of the deployment apparatus 30 is explained in detail below with reference to FIGS. 10 through 18.

Figure 3:
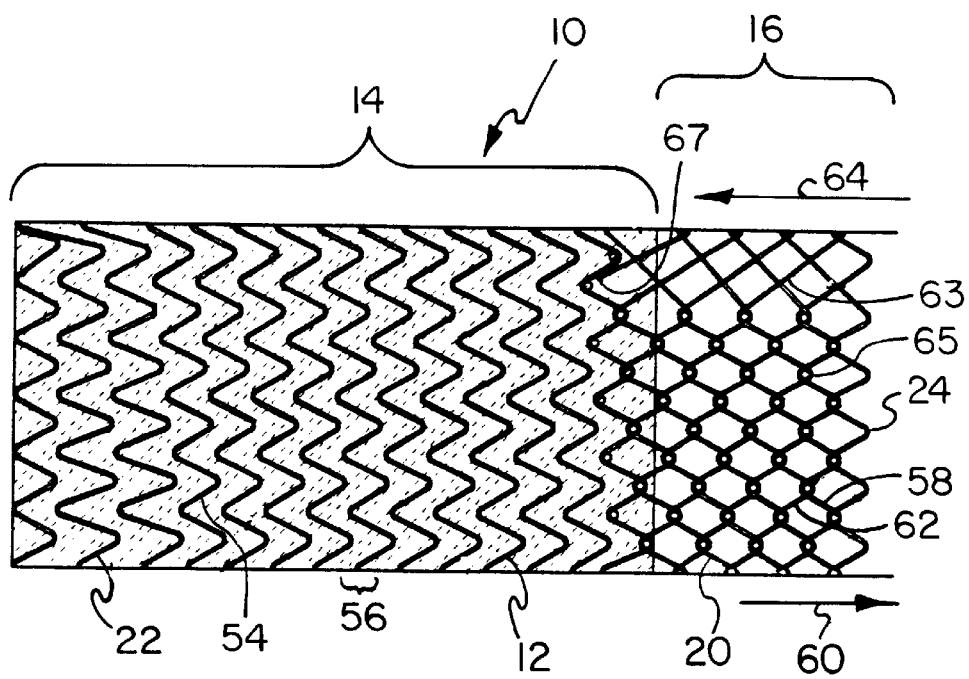
FIG. 3 is a top plan view of an endoprosthesis of the present invention, the endoprosthesis being normally cylindrical but is represented in this Figure flat by making a longitudinal cut along the length of the endoprosthesis and the uncoiling the endoprosthesis along this cut into a flat sheet. This view shows in detail the winding pattern of the two segments of the stent component of the endoprosthesis of the present invention.

The winding pattern of the preferred stent element 12 of the present invention is illustrated in FIG. 3. As can been appreciated through examination of this Figure, a single wire 22 may be employed to form both the first segment 14 and the second segment 16 of the stent element 12. Over the length of the first segment 14, the wire 22 may be formed in an undulated or serpentine pattern 54. Since the cover is used to maintain the relative positions of the first undulated pattern 54, each winding 56 of the undulated pattern around the circumference of the stent element 12 does not need to be attached to adjacent windings. It should be appreciated that some link, such as a fiber, wire extension, etc., may be employed to facilitate alignment of adjacent rows of windings if desired.

Along the length of the uncovered second segment 16, however, some means should be provided to prevent the second segment 16 from elongating in an uncontrolled fashion. In the preferred embodiment shown, this is accomplished by employing the interlocked (or "chain-linked") stent pattern 20. In this pattern the single wire 22 is wrapped from the first segment 14 to the distal end 24 and then back to the first segment 14. Along the length of the second segment 16 the wire 22 is provided with a second undulated pattern 58 along a first pass 60 and a third undulating pattern 62, interlocking with the second undulating pattern 58 along a second pass 64. By interlocking the second undulating pattern 58 and the third undulating pattern 62, the stent pattern 20 permits the second segment 16 to be longitudinally compressed, thus imparting flexibility; but the stent pattern prevents the second segment 16 from being longitudinally elongated beyond a predetermined maximum length. It should be noted that the interlocked stent pattern 20 also imparts columnar support when the device is in a radially compressed configuration and less so when it is deployed.

It is even more desirable for the interlocked stent pattern 20 along uncovered second segment 16 to provide some degree of resistance to longitudinal compression. This helps to prevent the second segment 16 from longitudinally collapsing upon itself once deployed in vivo. It has been determined that additional longitudinal stiffness may be provided to the second segment 16 by using a modified "cross-over" stent pattern 63 along one side of the second segment 16. As is shown, the cross-over pattern 63 links between every third row of the interlocked stent pattern 20. In other words, instead of the winding pattern linking the wire 22 with an adjacent row of the interlocked pattern, the wire 22 "crosses over" two wires and interlocks with a wire in a row two removed from the starting row. Any desired cross-over pattern may be incorporated without departing from the present invention, including one that skips one, two, three, four or more rows. The amount of longitudinal stiffness may be modified using this technique by skipping more rows to impart greater stiffness or skipping fewer rows to impart lesser stiffness.

Longitudinal stiffness may also be provided or supplemented by structures that will assist in holding the second segment 16 in an extended position. Stiffness may also be imparted by selectively binding portions of the interlocked pattern to each other using threads or wires or similar structures (for example, attaching interlocked junction 65 together with a thread that allows no, or only limited, actuation between pattern 58 and pattern 62).

There are a number of benefits achieved with the uncovered second segment 16 of the present invention. First, the stent patterns described above provide a clinically desirable amount of radial stiffness to the second segment 16. "Radial Stiffness" or "compressive stiffness" signifies the resistance of the endoprosthesis of the present invention to undergo circumferential compression. The testing parameters for radial stiffness are set forth in the Examples, below. Briefly, this value is the amount of force necessary to compress the device radially at a rate of 12.7 mm device circumference/ min to 75% of its original diameter with a 1 cm wide loop while the force is recorded. After completing the test, the slope of the load vs. displacement curve is calculated. This calculation is performed by recording the circumferential displacement and corresponding force at 5% and 20% diametric compression (i.e., the outer diameter of the stent is 95% and 80% of its original diameter loaded with a 0.05 Kgf load, respectively). Slope is then calculated by dividing the difference in these two forces by the differences in the corresponding displacements. The result, the slope from 5% to 20% diametrical compression of the force verses circumferential displacement, is then multiplied by pi (Π) to obtain the slope of the load vs. diameter curve, expressed in Kgf/mm device diameter.

It is preferred that the device of the present invention will have a radial stiffness of at least 0.1 Kgf/mm for the covered segment and at least 0.12 Kgf/mm for the uncovered segment. More preferably, the device should have a stiffness of at least 0.1, 0.12, 0.13, 0.14, 0.15, 0.16, 0.17, 0.18, 0.19, or 0.2 Kgf/mm or more for the covered segment, and 0.13, 0.14, 0.15, 0.16, 0.17, 0.18, 0.19, 0.2, 0.21, 0.22, 0.23, 0.24, or 0.25 Kgf/mm or more for the uncovered segment. The radial stiffness of the uncovered second segment 16 helps assure that the inlet to the shunt remains open in use. Additionally, since formation of the shunt is sometimes difficult to establish with accuracy, the radial stiffness of the second segment can assist in widening the portal vein or any collateral vein that might have been entered by accident.

Second, the open structure of the second segment allows for continued flow through the portal vein while simultaneously relieving excess pressure by way of the shunt. This is believed to be important for maintaining flow to the liver while also relieving excess pressures.

As has been noted, it is believed desirable that the endoprosthesis 10 of the present invention is highly resistant to any longitudinal elongation beyond its normal deployed length (that is, the longitudinal length of the device that it assumes upon deployment without tension applied to it). With respect to the uncovered second segment 16, it is desirable that the second segment 16 will resist any attempt to elongate it beyond about 25% of its normal deployed length. "Normal deployed length" comprises the length the second segment 16 naturally assumes when deployed on a table top, extended by hand to its fully extended length, and then released without being subjected to further elongation forces. More preferably, the second segment 16 resists elongation beyond about 20%, and even more preferably beyond about 15%, and still more preferably beyond 10%, of its normal deployed length. By the term "resist any attempt to elongate" beyond a given length, it is meant that the second segment 16 has a given maximum longitudinal length that will not be exceeded under normal conditions encountered once implanted. This can be tested in vitro by attaching the device to a 2 kg weight and allow the weight to hang under normal gravity for one (1) minute. The second segment 16 should not elongate more than 20% of its normal deployed length under these conditions.

The interlocked stent pattern 20, whereby the wire is doubled back on itself to form an interlocking pattern, provides a number of benefits. First, this winding pattern allows a single wire to be used in the stent element 12, avoiding possible manufacturing problems inherent in joining multiple wire components together. Second, this winding pattern allows the wire 22 to be terminated within the cover 18 and avoids having a loose end 67 of the wire 22 exposed at distal end 24 of the endoprosthesis 10. It should be appreciated that this minimizes the risk that the loose wire end 67 might snag or cause damage to the vascular system and eliminates the need for a separate manufacturing step to terminate the wire at the distal end 24 of the stent element 12. Third, the second segment 16 of the stent is very flexible, allowing it to be easily bent over a 90° angle with a 2 cm outer circumference. Fourth, the second segment 16 of the endoprosthesis tends to rebound when it is compressed under a force and then the force is removed.

Figure 4:
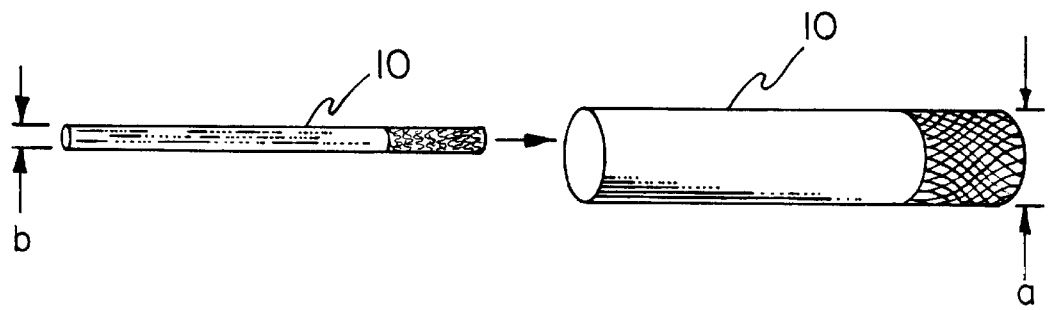
FIG. 4 is a side elevation view of an endoprosthesis of the present invention showing it in its compacted diameter (b) and in its enlarged deployed diameter (a)

As has been noted, it is believed important to provide an endoprosthesis for TIPS applications that includes both a stent element and a graft element in a single integral package that has a small compacted configuration (diameter) and fully operational deployed configuration (diameter). To this end, the present inventors have sought to create an endoprosthesis device that undergoes substantial growth between the compacted and deployed states. FIG. 4 illustrates one embodiment of a TIPS endoprosthesis 10 of the present invention showing it enlarging from a compacted diameter (b) to in an enlarged deployed diameter (a). It is desirable for the ratio of $$\frac{a}{b}$$

to comprise at least about 2, and more desirable for the ratio to comprise about 3 to 5 or more. The present invention employs a variety of unique materials and structures to produce highly compacted devices that can achieve these kinds of ratios.

Figure 5:
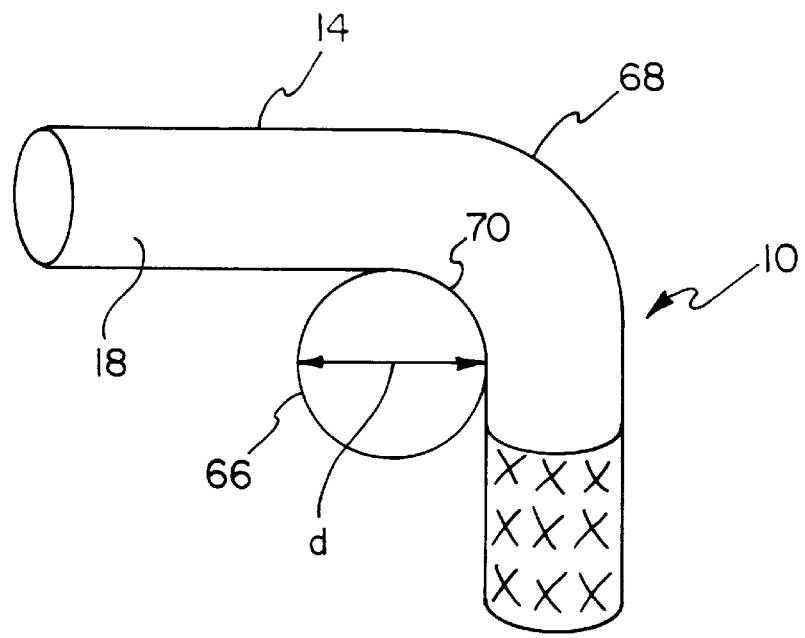
FIG. 5 is a side elevation view of an endoprosthesis of the present invention shown bent around a rod to demonstrate flexibility via bend radius.

Another useful attribute of the endoprosthesis device of the present invention is that it is constructed from materials that render the device highly flexible, both in its compacted and in its deployed configurations. In this regard, constructing the cover 18 from a stretchable material, such as the expanded PTFE material previously described, incorporates "stored length" of material into the device that allows the device to be readily bent without kinking. FIG. 5 shows a TIPS endoprosthesis 10 of the present invention bent around a rod 66 having a diameter "d." It is desirable that the first covered segment 14 of endoprosthesis 10 of the present invention be capable of being bent around a 25 mm diameter rod without kinking, and more preferably around a 20 mm diameter rod without kinking.

As the term "stored length" is used to describe the cover 18, it is intended to encompass the material comprising the cover either being elastic in nature and/or having sufficient excess material incorporated within the cover to allow an outer circumference 68 of the cover 18 to "stretch" without excessively buckling an inner circumference 70 of the cover 18. With the preferred cover material of the present invention, expanded PTFE, stored length may be achieved by compressing the node and fibril structure of the expanded PTFE in the normal deployed configuration of the device—allowing the outer circumference 68 to separate the node and fibril structure upon actuation around a rod while the inner circumference 70 remains compressed or undergoes further compression prior to buckling. Stored length can also be achieved by employing elastic materials such as polyurethane, silicone, or other biocompatible elastomers or porous materials, such as porous PET. Another suitable material is to construct the cover 18 from a stretchable material, such as an appropriately proportioned stetchable expanded PTFE disclosed in U.S. Pat. No. 4,877,661 to House, et al., incorporated by reference.

To determine the presence of "stored length" in a cover material of the present invention, a number of tests can be performed. First, the cover and device can be tested together to determine if the cover material possesses a recovery response whereby the cover will longitudinally elongate with the device when tensioned and then recover to, or close to, its original length upon release of tension. This can be tested by determining the "normal deployed length" of covered first segment 14 and then applying moderate longitudinal tension to the device to determine the maximum length the first segment will assume while recovering to near its original normal deployed length upon release of tension. To have "stored length" within the meaning of the present invention, the maximum length of the covered segment should be at least 5% more than the normal deployed length of the covered segment. More preferably, the maximum length of the covered segment should be 10, 15, or 20% or more of the normal deployed length of the covered segment.

Figure 23:
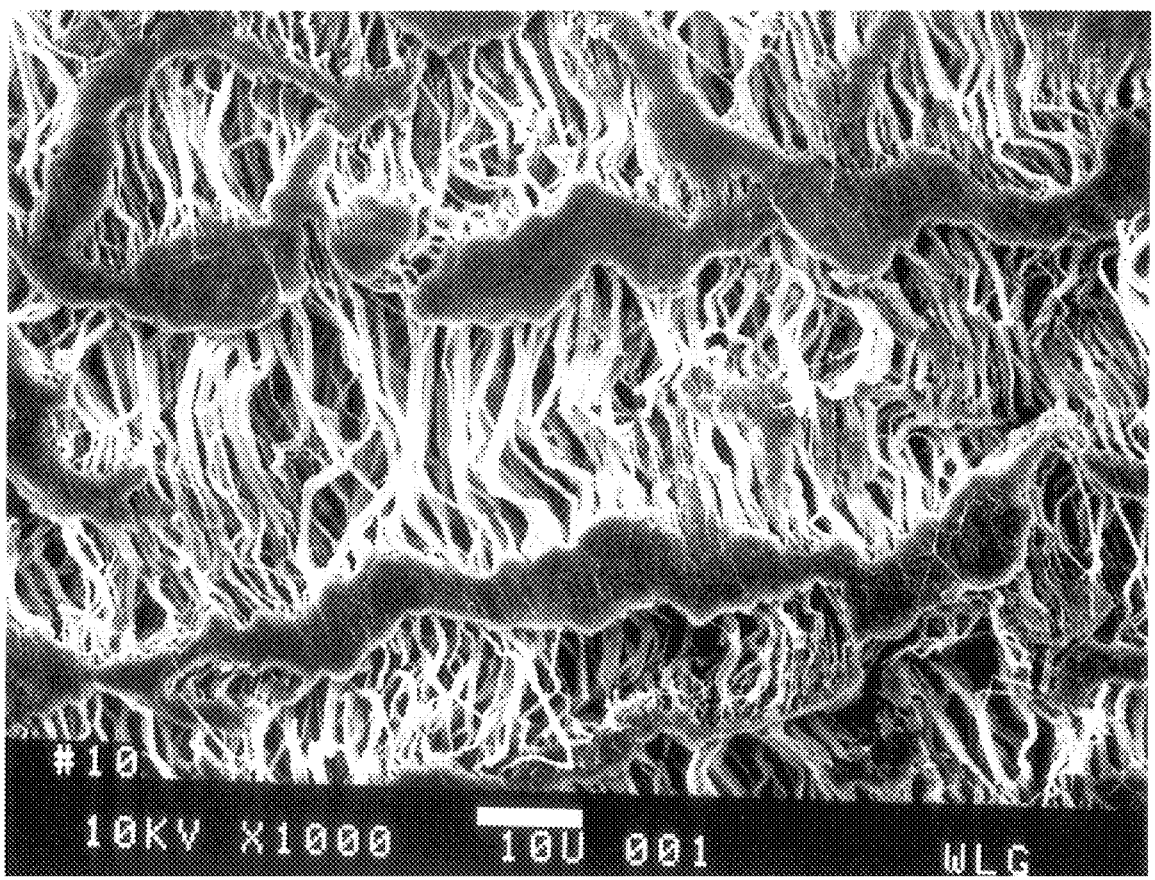
FIG. 23 is a scanning electron micrograph (SEM), enlarged 1000×, of the surface of an expanded polytetrafluoroethylene (PTFE) cover used in the present invention, having a node and fibril structure and having bent fibrils incorporated therein.

With respect to a cover constructed from expanded PTFE material, stored length can also be determined by microscopic analysis of the node and fibril structure of the material. As has been noted, an expanded PTFE material can have stored length imparted to it by "scrunching" the material and then heat treating it to heat set the fibrils into a bent configuration. An expanded PTFE material having bent fibrils is shown in the SEM of FIG. 23. When formed in this manner, the fibrils will straighten (thus lengthening the cover) when longitudinally tensioned and then returned to their bent configuration when released from tension (although the fibrils will "creep" into a straight configuration if tension is maintained over an extended period of time or the cover is exposed to high heat in its tensioned configuration). For an expanded PTFE material, the presence of "stored length" can be determined by examining the material untensioned to determined if the fibril structure is similar to that shown in FIG. 23. A test for this property is described in U.S. Pat. No. 4,877,661 to House, et al., incorporated by reference. Again, the maximum length of the covered segment with an expanded PTFE cover material should be at least 5% more than the normal deployed length of the covered segment, and more preferably 10, 15, or 20% or more of the normal deployed length of the covered segment.

The term "bent around a rod without kinking" is intended to encompass the endoprosthesis 10 being actuated to place its ends at a 90° angle with respect to each other, as is shown in FIG. 5, with no significant folding or buckling forming in the cover 18 at the point of bending around the rod 66. "Significant folding or buckling" is present when if there is a circumferentially directed crease along the inner circumference 70 that separates the creased portion of the endoprosthesis more than 1 mm from the rod. A similar test is described in detail in Section 8.9 of ANSI/AAMI VP 20-1994, incorporated by reference.

The compacting of the endoprosthesis 10 of the present invention may be accomplished through a variety of methods, as is illustrated in FIGS. 6a through 6d. FIG. 6a is an end view of a TIPS endoprosthesis of the present invention at its deployed diameter 72. Each of FIGS. 6b, 6c, and 6d illustrates how the endoprosthesis 10 may be compacted around a catheter 74 to achieve a compacted diameter 76. FIG. 6b is an end view of the TIPS endoprosthesis of FIG. 6a, with the endoprosthesis 10 shown compacted by folding and rolling the endoprosthesis 10. FIG. 6c is an end view of the TIPS endoprosthesis of FIG. 6a, with the endoprosthesis 10 shown compacted by radially compressing the endoprosthesis 10. FIG. 6d is an end view of the TIPS endoprosthesis of FIG. 6a, with the endoprosthesis 10 shown compacted by folding into pleats 78.

While each of these compacting techniques works well for many applications, it has been found that the covered first segment 14 of the stent element 12 of the present invention can catch on itself or the constraining sleeve 34 during deployment if the covered stent segment is not carefully handled. In this regard, as is explained in greater detail below, it is believed that compacting the TIPS endoprosthesis 10 of the present invention with multiple folds in the form of pleats 78, as shown in FIG. 6d, provides the best results.

FIG. 7 is a side elevation view of an undulated stent 80, shown in a deployed diameter 82 and in a compacted, pleated diameter 84. As can be seen, in the deployed diameter 80, the undulated stent pattern has exposed rearward facing apices 86 and forward facing apices 88. With apices facing in both forward and rearward directions, the inventors have found that there is a likelihood that the apices will catch and tangle a fibrous constraining sleeve. However, if the stent is compacted by pleating, one direction of apices can be formed within pleat 78 so that it is protected within the folded device below the level of the outer circumferential surface of the constrained device. This construction vastly reduces the risk of entanglement. In the compacted stent 84, it can be seen that only the forward facing apices 88 remain exposed on the outer circumference of the compacted device, while all of the rearward facing apices 86 are tucked within pleats 78 of the compacted device.

It should be noted that the pleated folding methods described herein can be used to direct apices into a wide variety of folded patterns. As such, the terms "forward" and "rearward" facing apices are used only for convenience to describe sets of apices that face in one direction or an opposite direction, without regard to the actual direction the device may ultimately be deployed.

It has been found that the endoprosthesis of the present invention can be compacted to its maximum degree, with a high compaction efficiency, and with minimal risk of apex entanglement if a pleated folding method is employed. One method of pleating an endoprosthesis is shown in FIGS. 8a, 8b, and 9.

Figure 8A:
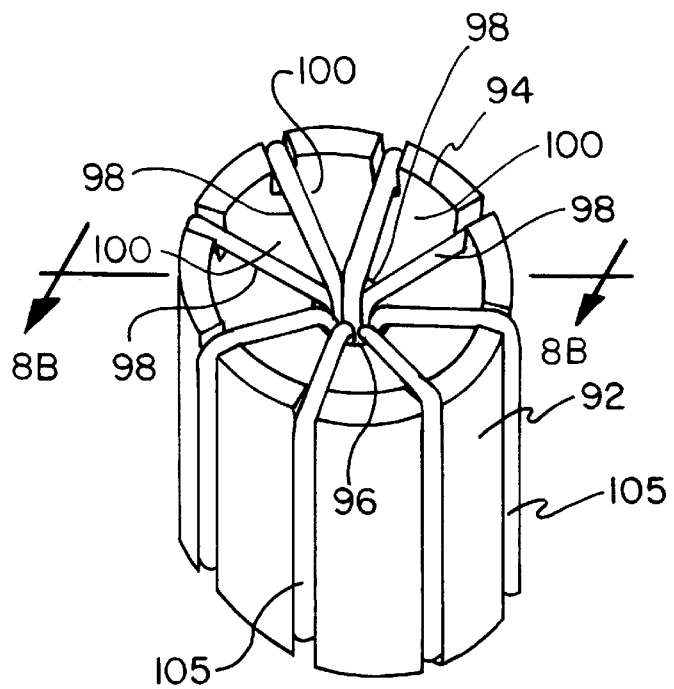
FIG. 8a is a three-quarter isometric view of one embodiment of a tapered die used to establish a pleated compacted endoprosthesis of the present invention.
Figure 8B:
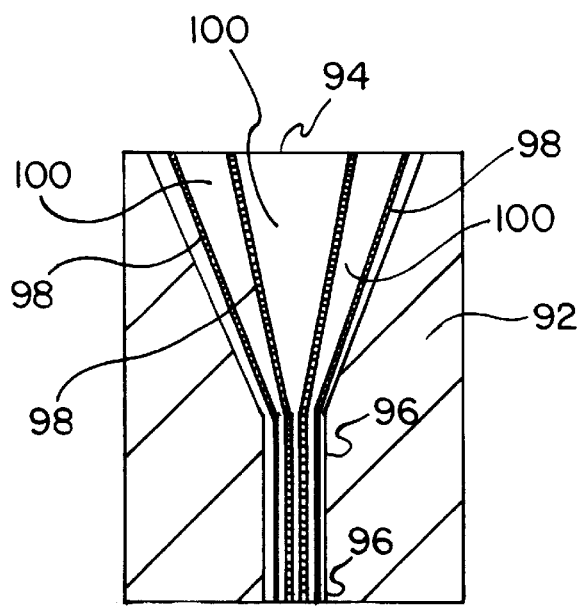
FIG. 8b is a side cross-section view of the tapered die of FIG. 8a along line 8b—8b.

FIGS. 8a and 8b illustrated a fluted tapered die 92 suitable for use in pleating a stent or stent-graft device. The tapered die 92 has a large opening 94 at one end and a small opening 96 at its opposite end. A number of raised flutes 98 are provided within the tapered die separated by grooves 100, each raised flute 98 corresponding to one desired pleat to be formed in the endoprosthesis. The raised flutes 98 and/or the grooves 100 may be formed by molding or machining the shapes into the die 92. Alternatively, as is illustrated, the flutes 98 may be formed by attaching one or more evenly spaced bands 105 per flute around the tapered die 92, such as by using polyester or nylon thread.

Figure 9:
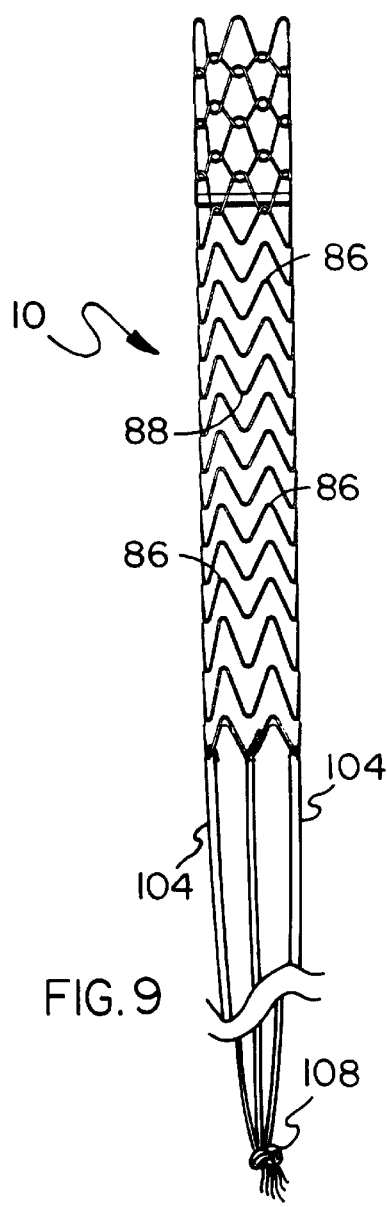
FIG. 9 is a side elevation view of an endoprosthesis of the present invention having tether lines positioned around the circumference of one end of the endoprosthesis in specific locations such as to control the locations where the stent forms pleats as it is drawn through a tapered die such as that shown in FIGS. 8a and 8b.

Compacting and pleating may be accomplished by attaching a series of tether lines 104 to an endoprosthesis 10, as shown in FIG. 9. The tether lines 104 may be formed from thin wires, polymer fibers, or other suitable materials. As is shown, the tether lines 104 are attached along the apices that are intended to remain exposed (in this case, forward facing apices 88). The tether lines 104 are centrally joined together at point 108.

To compact the device, the joined tether lines 104 are then drawn through the tapered die 92, exiting at small opening 96. Each of the tether lines 104 is drawn through a groove 100. In this manner, the tethered apices 106 will be folded outwardly and each of the untethered apices will be folded inwardly by the raised flutes 98 as the device is radially crushed. Once exiting the small opening 96, the compacted device can then be captured within a constraining sleeve or capture tube (not shown) for subsequent packaging. The constraining sleeve or capture tube may also contain means, such as longitudinal slots or grooves, to assist in maintaining the pleated compacted configuration of the endoprosthesis. Alternatively, it is also possible to pleat the device using a smooth tapered die with folding ridges (for example, longitudinally applied polyester lines) attached to the exterior of the endoprosthesis prior to compression. The folding ridges may then be removed following compression.

Figure 10:
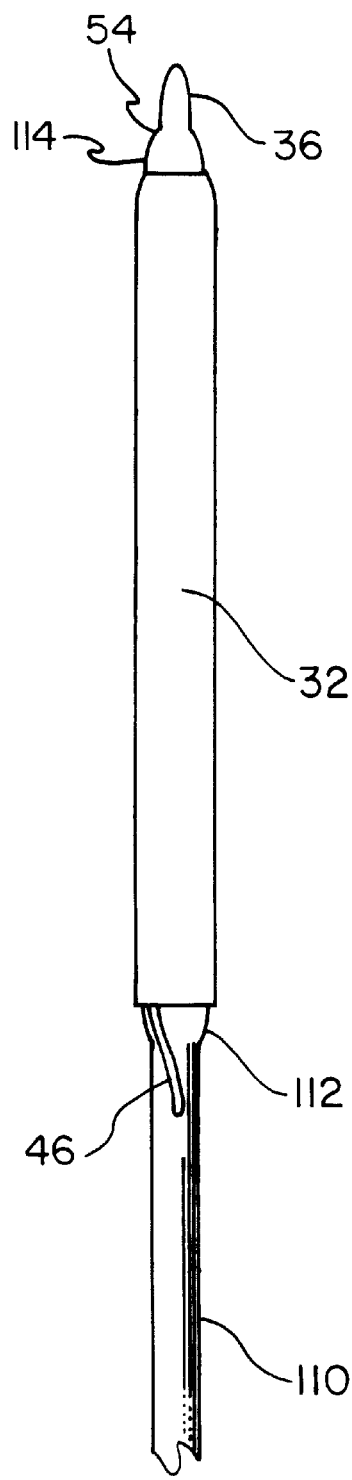
FIG. 10 is a side elevation view of a compacted endoprosthesis of the present invention mounted on a delivery catheter and covered with a packaging sheath.
Figure 11:
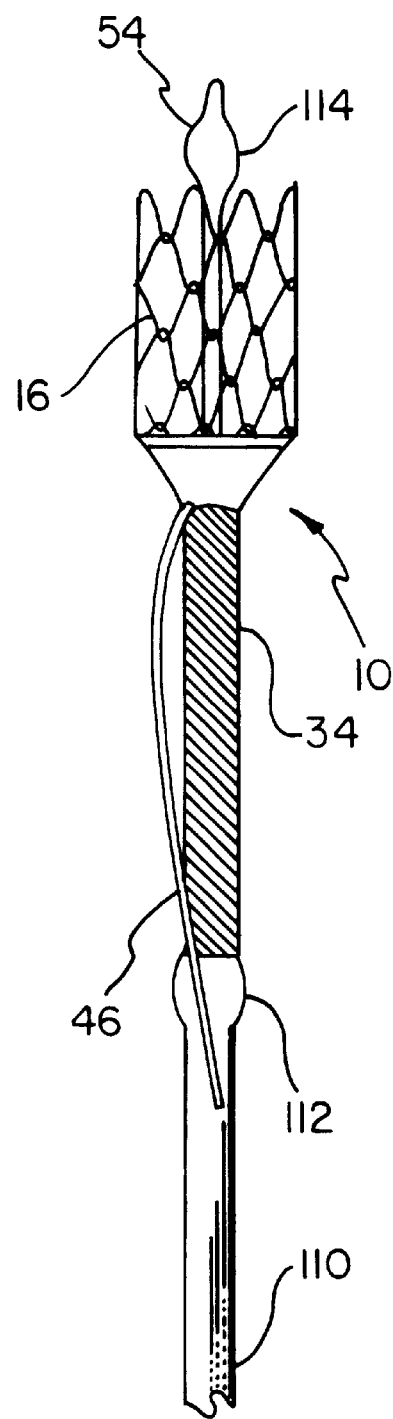
FIG. 11 is a side elevation view of a compacted endoprosthesis of the present invention shown partially deployed after the packaging sheath has been removed.

Packaging of the device of the present invention can be accomplished through a variety of methods. As should be appreciated from the following description of the preferred deployment method of the device of the present invention, it is preferred that the endoprosthesis 10 of the present invention be packaged to permit multi-stage deployment. One such method to accomplish this packaging is illustrated in FIGS. 10 and 11. FIG. 10 shows a device of the present invention as it is delivered for use. The endoprosthesis (not shown) is mounted on a delivery catheter 110 between two "olives" 112, 114. Olives are solid bumps of increased diameter on the catheter shaft (for instance, formed from a polymer, glass, or metal material) that inhibit the compacted endoprosthesis from sliding on the catheter shaft. Olive 114 at the distal shaft 36 may contain a radiopaque marker 54 to aid in positioning of the device. An introducing sleeve 32 is attached over the endoprosthesis. The introducing sleeve 32 is preferably made of polyethylene or similar material with its inner diameter being approximately equal to the outer dimensions of the compacted endoprosthesis. One or more markers or mechanical stops may be provided on the introducing sleeve 32 to aid in initial positioning and deploying. A deployment line 46 can be seen exiting the introducing sleeve 32 and passing into the delivery catheter 110 (as was previously explained in reference to FIG. 2, the deployment line 46 exits the delivery catheter at the deployment port 42).

When the introducing sleeve 32 is removed, as is shown in FIG. 11, the second segment 16 of the endoprosthesis 10 will expand to close to its fully deployed diameter. The remainder of the endoprosthesis 10, however, is contained within a constraining sleeve 34. In operation, the constrained device will pass from the introducing sleeve 32 into a catheter tube (of approximately equal inner diameter) extending past the ultimate deployment site. Deployment of the second segment 16 will occur when the device is separated from the catheter tube at the deployment site.

The preferred constraining sleeve comprises a plurality of interwoven threads, such as that disclosed in U.S. patent application Ser. No. 09/098,103, filed Jun. 15, 1998, to Armstrong et al., incorporated herein by reference. The constraining sleeve 34 can be separately deployed by actuating deployment line 46.

While the multi-stage deployment apparatus illustrated in FIGS. 10 and 11 comprises the preferred embodiment of deployment of the present invention, it should be appreciated that different embodiments may achieve similar results. For instance, the second segment 16 may be contained in its own constraining apparatus, such as the fibers used in constraining sleeve 34 or other constraining devices or other materials. Conversely, the constraining sleeve 34 may be formed from a tubular material (like the introducing sleeve 32). Additionally, it may be beneficial under certain circumstances to provide more than a two-stage deployment, such as be providing multiple constraining sleeves that permit multiple stage deployment of the first segment 14 of the endoprosthesis 10.

The operation of the endoprosthesis and deployment apparatus of the present invention can be appreciated through the following description illustrated by FIGS. 12 through 18.

Figure 12:
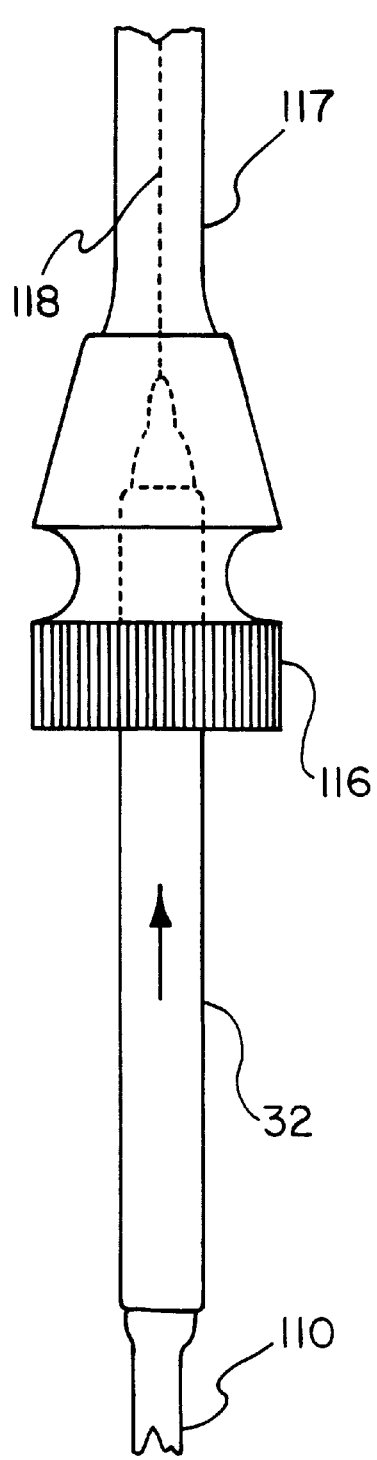
FIG. 12 is a side elevation view of the compacted endoprosthesis of FIG. 10 with the packaging sheath and delivery catheter being inserted through a hemostatic sheath.

FIG. 12 illustrates a compacted endoprosthesis of the present invention, mounted within introducing sleeve 32, being inserted through a hemostatic valve 116 into catheter tube 117. The catheter tube 117 has previously been advanced into the portal vein. A guide wire 118 may be provided to assist in device placement.

Figure 13:
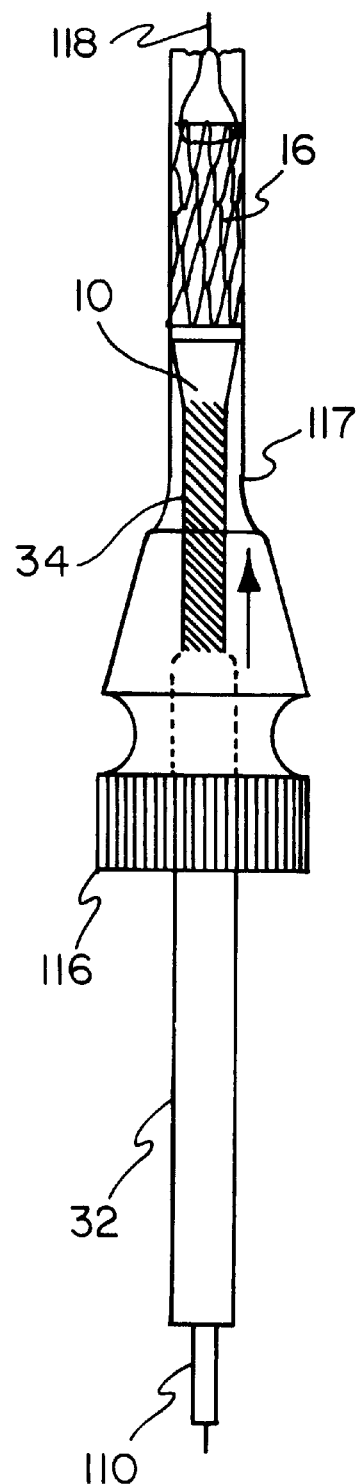
FIG. 13 is a side elevation view of the endoprosthesis of FIG. 12 with the delivery catheter partially advanced into a transjugular sheath with the packaging sheath shown partially removed.

As is shown in FIG. 13, the endoprosthesis 10 is advanced out of the introducing sleeve 32 and into catheter tube 117. The delivery catheter is then advanced to cause the second segment 16 to become constrained within catheter tube 117.

As is illustrated in FIGS. 14 and 15, the endoprosthesis 10 is then advanced through the catheter tube 117 through the inferior vena cava 119a, the hepatic vein 119b, the intrahepatic tract (shunt) 120 formed in the liver 122, and well into the portal vein 124. Radiopaque tip 54 can be aligned with the end of the catheter tube 117. The radiopaque marker 28 can be positioned distal to the intrahepatic juncture site 126.

Figures 16, 17:
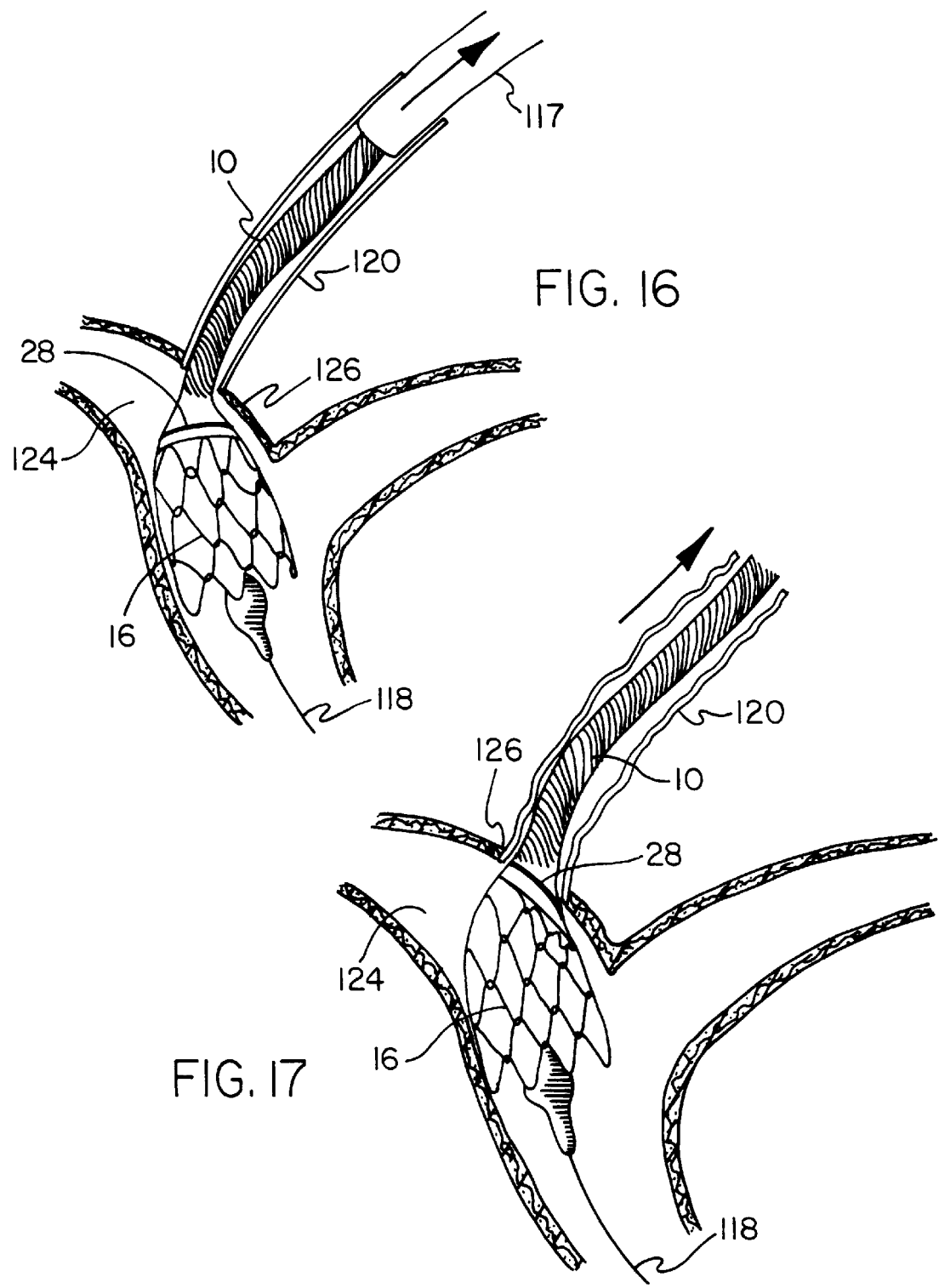
FIG. 16 is a side elevation view of a TIPS endoprosthesis of the present invention being partially deployed in the portal vein through withdrawal of the hemostatic sheath.
FIG. 17 is a side elevation view of the TIPS endoprosthesis of the present invention being partially withdrawn to properly position the endoprosthesis within the portal vein, an unconstrained expanded portal stent segment of the endoprosthesis engaging the intrahepatic juncture to assure proper placement.

In FIG. 16 the catheter tube 117 is withdrawn proximally, which permits the second segment 16 to fully expand within the portal vein 124. As is shown in FIG. 17, the delivery catheter 110 is then withdrawn through the catheter tube 117 until the unconstrained second segment 16 engages the intrahepatic juncture 126. Alignment can be confirmed fluoroscopically by correct orientation of marker band 28 with or without confirmatory injections of radiopaque contrast media.

Figure 18:
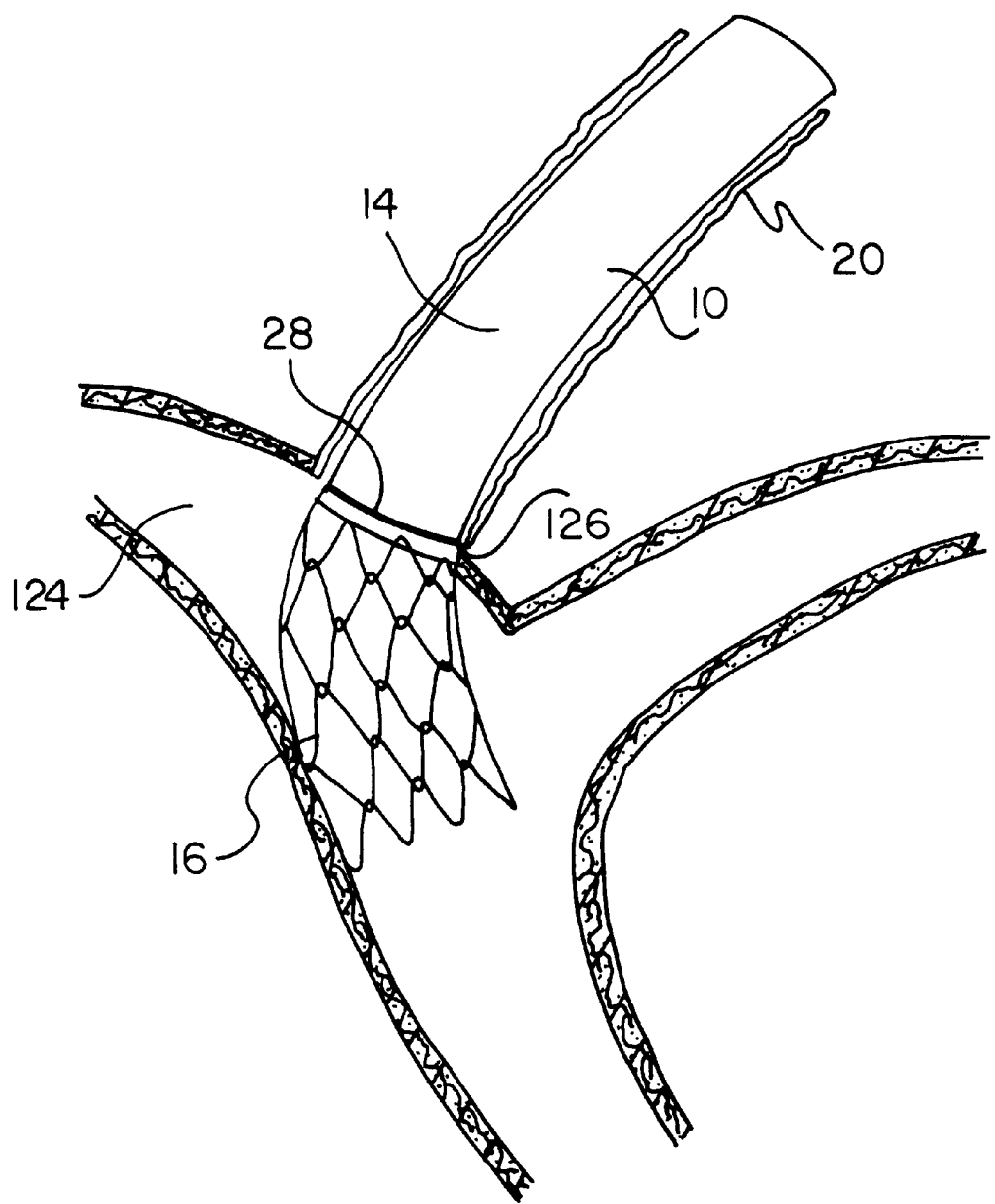
FIG. 18 is a side elevation view of the TIPS endoprosthesis of the present invention having been fully deployed within an intrahepatic tract and the portal vein.

As is illustrated in FIG. 18, once the device is properly aligned, the constraining sleeve 34 is removed by actuating deployment line 46, allowing the first segment 14 of the endoprosthesis 10 to fully enlarge in place in a tip-to-hub direction. If desired, further touch-up of the endoprosthesis 10 can be performed by subsequent balloon dilation of the endoprosthesis 10.

It should be appreciated that the above deployment procedure aligns the covered portion of the endoprosthesis within the intrahepatic tract (shunt) 120. Further, the uncovered second segment 16 permits blood flow both to enter the shunt 120 and to continue through the portal vein 124. The result is that excess pressure can be relieved from the portal system (through the shunt) without completely eliminating normal blood flow through portal vein 124.

Without intending to limit the present invention to the specifics described hereinafter, the following examples illustrate how the present invention may be made.

EXAMPLE 1

A pin jig is manufactured by turning 304 stainless steel rod stock to an 8 mm diameter. Holes are then drilled in the mandrel (#67 bit) to create the pattern to wind the stent depicted in FIG. 3, with 5 forward facing apices (10 holes) per revolution. Beyond each end of the hole pattern on the mandrel, holes are drilled and tapped to fit 10–32 screws. 1/32 inch (0.79 mm) diameter ×4 mm length steel pins are then place into these holes, such that 2 mm of the pins are imbedded in the mandrel.

Nitinol wire of a 0.010" (0.25 mm) nominal diameter (acquired from Nitinol Devices and Components, Fremont, Calif.) is then wound by hand around this pin jig in the pattern shown in FIG. 3 and the ends of the wire affixed in a tight configuration to the mandrel by 10–32 screws. The wire and the mandrel is then set in a convection oven set a 450° C. for 15 minutes, followed by a rapid quench in ambient temperature water. After the mandrel is allowed to cool, the wire stent is removed from the mandrel by removing the pins and sliding the stent from the mandrel.

Next, as a manufacturing aid to assist in alignment of apices relative to each other, a small diameter expanded PTFE filament (for example, CV-8.0 suture available from W. L. Gore & Associates, Inc., Flagstaff, Ariz., USA) is tied to the end of the wire on the proximal end of the device 30. The filament is spirally wound toward the distal end of the device 24. The filament is wound through apices of adjacent rows of the stent structure. A similar winding alignment procedure is described in PCT Application PCT/US96/19669 to Martin et al., incorporated herein by reference. The filament is wound along the length of the first segment 14, where it may then be fixed to the terminal end of the stent wire 67. This winding procedure may be started at either end 24 or 30 of the stent with similar results.

Next, a thin-walled expanded PTFE tubular extrusion (wall thickness 0.004 inch (0.1 mm)), as previously described is then circumferentially wrapped with five to seven layers of an expanded PTFE film. The expanded PTFE film has a thickness of 0.0007" (0.02 mm), a density of 0.7 g/cc, and a methanol bubble point of 3 psi (21 KPa).

This construction is heat treated for 15 minutes at 370° C. and cooled. The wrapped tube is then removed from the mandrel.

Another thin-walled expanded PTFE tube is placed into the lumen of the wrapped tube. These two tubes are then fitted over an 8 mm mandrel. The wrapped expanded PTFE tube is then over-wrapped with another layer of the expanded PTFE film.

The construction is then compressed longitudinally by hand to approximately a third of its original length. The construction and mandrel are then heat treated at 320° C. for 10 minutes, removed from the oven, and allowed to cool. The outer over-wrap is removed. The construction is then removed from the mandrel and the graft placed under moderate tension to restore the graft to approximately ⅔rds of its original length.

After trimming one end of the construction squarely, the stent is slid on the outside of the PTFE construction and the end of the interlocked section of the stent (see FIG. 1) aligned with the squared end such that one row of interlocked apices is covered. The 8 mm mandrel is then inserted into the PTFE/nitinol construction. The stent apices are then manually adjusted to achieve even spacing of the apices, with the forward facing apices from each row aligned longitudinally. A PTFE/FEP film, as previously described, is then over-wrapped with the FEP side down on the exterior surface of the section of the stent with non-interlocked windings. This PTFE/FEP film comprises an expanded layer of PTFE film with a discontinuous layer of FEP. The film has a thickness of 0.0005 inch (0.01 mm) and a methanol bubble point of 1.2 psi (8 KPa). This wrap is a continuous helical circumferential wrap with overlapping edges to produce approximately 3–5 layers.

After completing the wrap, the wrap is spot attached using a soldering iron with a tip temperature of sufficient heat to melt the FEP. A sacrificial compression wrap is then applied by helically wrapping with moderate tension an expanded PTFE film circumferentially around the exterior of the construction. The construction is then heat treated at 320° C. for five minutes and allowed to air cool. After the construction has cooled, the over-wrap is removed. The construction is again longitudinally compressed approximately 50% of its original length, making sure that the apices remained aligned. The construction is over-wrapped with a thin expanded PTFE film that serves as a compression layer and heat treated at 320° C. for 10 minutes. After a short air cool, while the tube is still warm, moderate longitudinal tension is applied to the device by hand to pull the entire device out to approximately its original length. The excess expanded PTFE tube is then trimmed flush with the stent end.

Threads are attached to the covered end of the device by piercing through the cover material at each end apex of the device with a needle. Thread is fed through these holes to form loops, and about a 30 cm from the device they are tied together with even slack. The knotted end of the threads is fed sequentially though a PTFE tapered die into a PTFE capture tube. The tapered die is constructed with an approximate 15° included angle taper and had five nylon lines (outer diameter=0.018" (0.46 mm)) positioned approximately equal distance (i.e., 72°) around the inner circumference of the taper, as is shown in FIG. 8a. The devices and tapered die are then sprayed with a refrigerant (MicroFreeze, Micro-Care Corporation, Bristol Conn.) to reduce the temperature of the device below the nitinol's martinsitic temperature. The device is immediately drawn through the tapered die into a PTFE capture tube. As the endoprosthesis is drawn through the die, a 0.055 inch (1.4 mm) outer diameter polyethylene shaft is placed within its lumen. The resulting device can then be removed from the capture tube.

The deployed device is flexible in both the covered and uncovered portions. The uncovered portion can be compressed longitudinally, and the stent elastically recovers close to its original length when the digital pressure is removed. The permeability of the covered portion of the construction is low and the hoop strength of the device is substantial. The device is compressed such that the apices pointing away from the attached threads are tucked under the apices pointed toward the thread. This compression technique results in a small collapsed profile.

Tests performed on this example include:

Kink Diameter

This device is bent at room temperature around progressively smaller diametrical mandrels until a kink formed in the covered graft section. The smallest diameter at which that device did not kink was recorded. A "kink" is present when if there is a crease along the inner circumference 70 that separates the creased portion of the endoprosthesis more than 1 mm from the rod. A similar test is described in detail in Section 8.9 of ANSI/AAMI VP 20- 1994, incorporated by reference, although the current test is performed without internal pressure.

Transmural Permeability

To quantify a level of "bile resistance," the inventors used a measure of air resistance described by Tappi Standard T 460 om-88 in order to establish a "Gurley Number." The measurement was performed using a GURLEY™ Densometer Model 4110 permeability tester available from Teledyne (Troy, N.Y., USA). Briefly, the tester measures the time that is takes to pass 100 cubic centimeters of ambient temperature air through an orifice with a pressure of 4.9 inches of $H_2O$(1.2 kPa).

Figure 19:
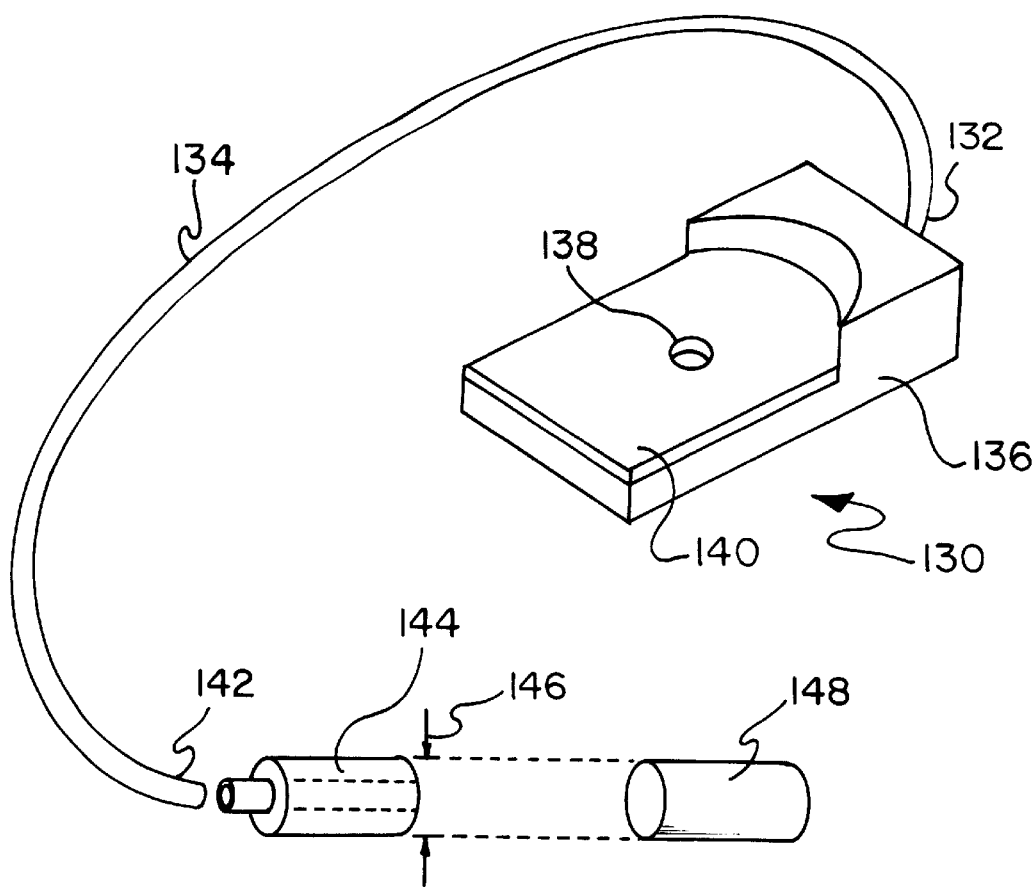
FIG. 19 is a three-quarter isometric view of a portion of an apparatus used to test the permeability of the cover of the present invention.
Figure 20:
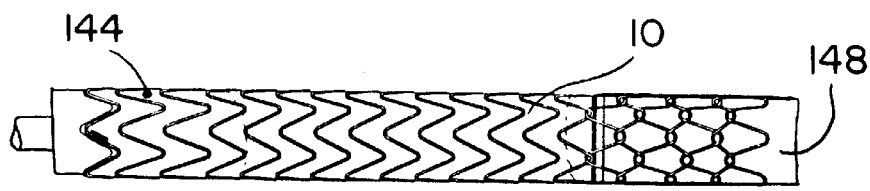
FIG. 20 is a side elevation view of an endoprosthesis of the present invention mounted with the fixture elements illustrated in FIG. 19.

The fixture apparatus 130 used to test for the "Gurley Number" is shown in FIG. 19. A first end 132 of a flexible tube 134 is attached to an adapter 136. The adapter 136 is attached to the Densometer via a 25.4 mm diameter circular plate (not shown) that attaches to the adapter 136 via orifice 138. Sealing material 140 (e.g., a ⅛ inch (0.32 mm) thick silicone sheet) is mounted around the orifice 138 to effectuate a seal with the circular plate. This assures that the air measured by the Densometer passes through orifice 138. A second end 142 of the flexible tube 134, which is in direct communication with orifice 138, is attached to a circular fitting 144. The circular fitting 144 has an outer diameter 146 approximately the same as the inner diameter of the device 10 to be tested. The circular fitting 144 is attached to the device 10, as is shown in FIG. 20, using PTFE pipe thread tape to create an air tight fitting around the circumference. A sealing plug fitting 148 is provided to attached to the opposite end of the device 10 to completely seal the second segment 16 and seal a portion of the first segment 14, as these elements are illustrated in FIG. 1.

The resistance to flow through each of the fittings with no sample attached is measured to 1.5 seconds or less per 100 cc of air, which is significantly less time than all of the samples measured. Prior to taking a measurement, the test area is calculated by multiplying the separation of the fittings to which the sample was attached to the inner circumference of the sample. After measuring the time for 100 cubic centimeters of air to pass through the sample, this value is normalized by multiplying by the total area tested. The test areas generally range from 4 to 16 $cm^2$, and multiple test areas are tested for each sample.

Radial Compression Testing

Figure 21:
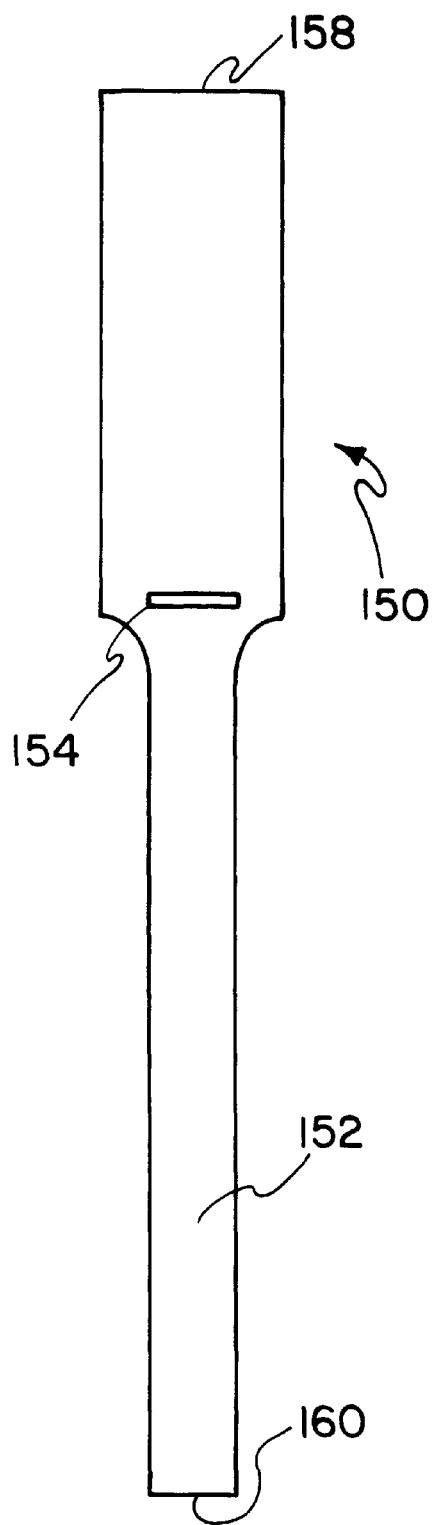
FIG. 21 is a top plan view of a loop device used to measure radial stiffness of an endoprosthesis of the present invention.
Figure 22:
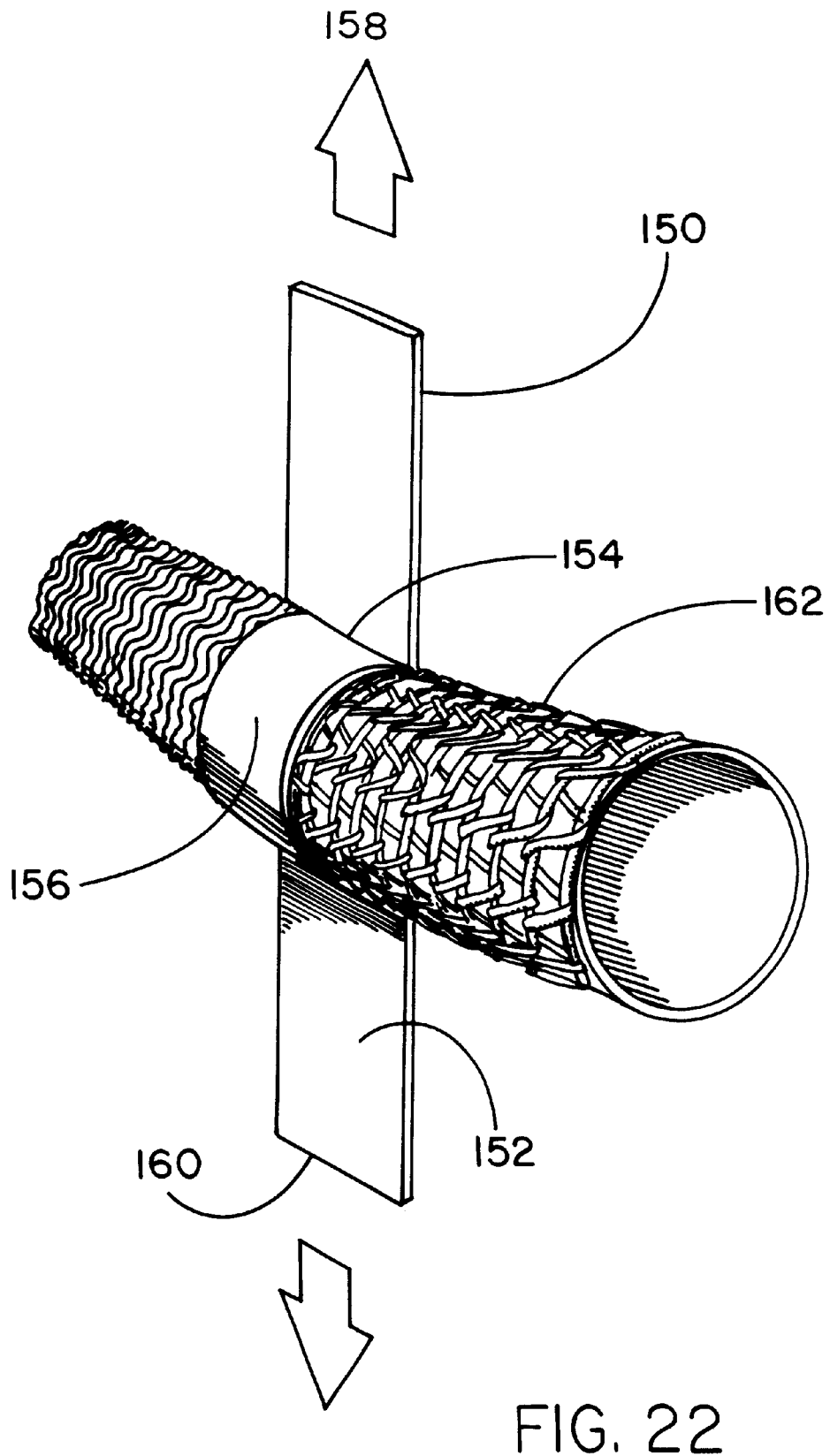
FIG. 22 is a three-quarter perspective view of an endoprosthetic device mounted in the loop device of FIG. 19, positioned so as to connect the loop device to a tensile tester.

Compression testing is performed using an INSTRON tensile testing machine equipped with a heated test chamber set to 37° C. As is shown in FIGS. 21 and 22, a loop compression fixture 150 is fabricated using 0.1 mm thick polyester film. The film is cut into a 20 mm×160 mm rectangle. On one end of the rectangle, 5 mm is trimmed from each side from the end for 100 mm, creating an elongated tab 152. Approximately 5 mm past the trimmings in the wide section, a slit 154 (approximately 11 mm×1 mm) is cut in the film to fit the tab 152. The 1-cm wide tab 152 is then. looped through the slit 154 to form a variable diameter loop 156. After forming the loop 156, ends 158, 160 of the film are placed in opposing tensile testing grips of the tensile tester.

Devices to be tested are heated to 37° C. for greater than 30 minutes immediately prior to the testing. Inside the loop 156 is placed a device 162 to be tested and the opposing jaws separated until a pre-load of 0.05 kg on the variable diameter loop is detected. The device is then compressed at a rate of 12.7 mm device circumference/min to 75% of its original diameter while the force is recorded. After completing the test, the slope of the load vs. displacement curve is calculated. This calculation is performed by recording the circumferential displacement and corresponding force at 5% and 20% diametric compression (i.e., the outer diameter of the stent is 95% and 80% of its original diameter loaded with a 0.05 load, respectively). Slope is then calculated by dividing the difference in these two forces by the differences in the corresponding displacements. The result, the slope from 5% to 20% diametrical compression of the force verses circumferential displacement, is then multiplied by pi (Π) to obtain the slope of the load vs. diameter curve, expressed in kg/mm diameter.

Profile

Profile is equal to the inner diameter of the PTFE capture tube into which the device is drawn. Within the lumen of the device constrained in the PTFE capture tube is a 0.055 inch (1.4 mm) outer diameter polyethylene tube to represent the catheter that the device is loaded.

Scanning Electron Microscope Photomicrographs/Bent fibrils

Scanning electron microscope photomicrographs (SEMs) are taken of the luminal surface. Bent fibrils are measured in a manner consistent with that method taught in U.S. Pat. No. 5,308,664 to House et al. Briefly, horizontal lines are drawn on the SEM photomicrographs (3 lines per photo, 3 photos per sample) (total of 9 measurements taken). Horizontal distances (H) are measured between nodes along this line. Vertical distances (V) of the bent fibrils are measured from the horizontal line. A ratio (V/H) is calculated and recorded. An SEM of a cover of the present invention showing bent fibrils therein is attached as FIG. 23.

Internal Corrugations

The internal corrugations of the graft are measured using gauge pins. Gauge pin testing is accomplished by first testing the internal diameter with pins until the fit between the pin and internal diameter allows the pin to be lifted when suspending only the device. Next, the device is longitudinally compressed approximately 10% (to simulate bending)

and the pin test is repeated. The percent of the compressed inner diameter to the non-compressed inner diameter is then calculated.

8 mm Device

Testing is perform as described above, with the following results:

| | |
|---|---|
| Kink Diameter | 24 mm |
| Radial Stiffness | Covered section - 0.137 kg/mm$_{diameter}$ |
| | Uncovered section - 0.193 kg/mm$_{diameter}$ |
| Permeability | 213 sec per 100 cc air per 1 cm$^2_{material}$ |
| Profile | 3.2 mm |
| Bent Fibrils | Average ratio V/H = 0.131 |
| Internal Corrugation | 96% of original |

EXAMPLE 2

A device similar to the one in described in Example 1 is made, however, the inner diameter is 10 mm, the stent pattern has 6 apices per revolution, the wire diameter is 0.011 inches (0.28 mm), and the tapered die has 6 nylon lines (spacing=60°). Testing is perform as described above, with the following results:

10 mm Device

| | |
|---|---|
| Kink Diameter | 20 mm |
| Radial Stiffness | Covered section - 0.173 kg/mm$_{diameter}$ |
| | Uncovered section - 0.258 kg/mm$_{diameter}$ |
| Permeability | 143 sec per 100 cc air per 1 cm$^2_{material}$ |
| Profile | 3.6 mm |
| Bent Fibrils | Average ratio V/H = 0.176 |
| Internal Corrugation | 99% of original |

EXAMPLE 3

A device similar to the one in Example 1 is made; however, the inner diameter is 12 mm, the stent pattern has 6 apices per revolution, the wire diameter is 0.010 inches (0.25 mm), and the tapered die has 6 nylon lines (spacing= 60°). Testing is performed as described above, with the following results:

12 mm Device

| | |
|---|---|
| Kink Diameter | 24 mm |
| Radial Stiffness | Covered section - 0.103 kg/mm$_{diameter}$ |
| | Uncovered section - 0.157 kg/mm$_{diameter}$ |
| Permeability | 111 sec per 100 cc air per 1 cm$^2_{material}$ |
| Profile | 3.6 mm |
| Bent Fibrils | Average ratio V/H = 0.234 |
| Internal Corrugation | 98% of original |

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. An endoprosthesis comprising:
   self-expanding stent element having at least a first segment and a second segment;
   a cover on the first segment, with the second segment being left uncovered;
   the uncovered second segment including a stent pattern that prevents uncontrolled longitudinal elongation of the second segment of the stent;
   the cover including a structure having a transmural permeability time over a majority of the cover of greater than 60 seconds per 100 cc of air per 1 cm$^2$ of cover at 1.2 kPa of pressure;
   wherein the stent pattern comprises a continuous wire wrapped across the second segment at least twice producing interlocked apices and at least one crossover region; and
   wherein the wire includes two ends and the two ends are both terminated within the covered first segment.

2. The endoprosthesis of claim 1 wherein the cover comprises a graft element having a stored length.

3. The endoprosthesis of claim 2 wherein the cover has a wall thickness of less than 0.4 mm.

4. The endoprosthesis of claim 1 wherein the prosthesis has
   a deployed diameter of "a";
   a compacted diameter of "b";
   wherein a ratio of $$\frac{a}{b}$$

comprises at least 2.

5. The endoprosthesis of claim 4 wherein the cover has a wall thickness of not more than 0.4 mm.

6. An endoprosthesis of claim 1 wherein the first segment forms 90° bend around a 24 mm diameter rod without kinking.

7. The endoprosthesis of claim 1 wherein the cover comprises a polytetrafluoroethylene graft component.

8. The endoprosthesis of claim 1 wherein the endoprosthesis is crushed down to assume a compacted diameter, the endoprosthesis having folds in its compacted diameter.

9. The endoprosthesis of claim 1 wherein the endoprosthesis is crushed down to assume a compacted dimension, the endoprosthesis having folds in its compacted dimension that arrange apices facing in one direction below an outer surface of the compacted dimension of the device.

10. The endoprosthesis of claim 1 wherein
    the endoprosthesis is self-expanding;
    the endoprosthesis is compacted for introduction; and
    the endoprosthesis is held in its compacted state by deployment means, the deployment means permitting multi-stage deployment of the endoprosthesis.

11. The endoprosthesis of claim 1 wherein the cover comprises a material that is resistant to bile permeation.

12. The endoprosthesis of claim 1 wherein the stent pattern of the second segment comprises a helical chain link pattern.

13. The endoprosthesis of claim 12 wherein the helical chain link pattern is formed from a single wire that is wrapped across the second segment in one longitudinal direction and then wrapped across the second segment again in an opposite longitudinal direction, the wire being interwoven with itself to form the chain link pattern.

14. The endoprosthesis of claim 1 wherein the second segment has a length and the second segment is highly resistant to longitudinal elongation of more than 20% of its length.

15. The endoprosthesis of claim 1 wherein the first segment of the stent is attached to the cover so as to resist uncontrolled longitudinal elongation of the first segment.

16. An endoprosthesis comprising:
    a self-expanding stent element having at least a first segment and a second segment;

a cover on the first segment, with the second segment being left uncovered;

the uncovered second segment including a stent pattern that prevents uncontrolled longitudinal elongation of the second segment of the stent;

wherein the stent pattern comprises a continuous wire wrapped across the second segment at least twice producing interlocked apices and at least one crossover region; and wherein the wire includes two ends and the two ends are both terminated within the covered first segment.

17. The endoprosthesis of claim 16 wherein the cover includes a structure having a transmural permeability time over a majority of the cover of greater than 60 seconds per 100 cc of air per 1 cm$^2$ of cover at 1.2 kPa of pressure.

18. An endoprosthesis comprising:

a self-expanding stent element having at least a first segment and a second segment;

a cover on the first segment, with the second segment being left uncovered;

the uncovered second segment including a stent pattern that prevents uncontrolled longitudinal elongation of the second segment of the stent;

the cover including a structure having a transmural permeability time over a majority of the cover of greater than 60 seconds per 100 cc of air per 1 cm$^2$ of cover at 1.2 kPa of pressure;

wherein the stent pattern of the second segment comprises a helical chain link pattern; and wherein the helical chain link pattern is formed from a single wire that is wrapped across the second segment in one longitudinal direction and then wrapped across the second segment again in an opposite longitudinal direction, the wire being interwoven with itself to form the chain link pattern.

* * * * *